US011207540B2

(12) United States Patent
Zangen et al.

(10) Patent No.: US 11,207,540 B2
(45) Date of Patent: Dec. 28, 2021

(54) ELECTROMAGNETIC COIL ASSEMBLY

(71) Applicant: BRAINSWAY LTD., Jerusalem (IL)

(72) Inventors: Abraham Zangen, Jerusalem (IL); Yiftach Roth, Rechelim (IL)

(73) Assignee: BRAINSWAY LTD., Jerusalem (IL)

( * ) Notice: Subject to any disclaimer, the term of this patent is extended or adjusted under 35 U.S.C. 154(b) by 0 days.

(21) Appl. No.: 16/965,058

(22) PCT Filed: Feb. 5, 2019

(86) PCT No.: PCT/IL2019/050136
§ 371 (c)(1),
(2) Date: Jul. 27, 2020

(87) PCT Pub. No.: WO2019/150378
PCT Pub. Date: Aug. 8, 2019

(65) Prior Publication Data
US 2021/0106842 A1    Apr. 15, 2021

(30) Foreign Application Priority Data

Feb. 5, 2018  (CN) ......................... 201820199640.3
Feb. 5, 2018  (CN) ......................... 201820203002.4

(51) Int. Cl.
*A61N 2/02* (2006.01)
*A61N 2/00* (2006.01)
*H01F 27/06* (2006.01)
*H01F 27/28* (2006.01)

(52) U.S. Cl.
CPC .............. *A61N 2/02* (2013.01); *A61N 2/006* (2013.01); *H01F 27/06* (2013.01); *H01F 27/28* (2013.01)

(58) Field of Classification Search
CPC ................................ A61N 2/006; A61N 2/02
See application file for complete search history.

(56) References Cited

U.S. PATENT DOCUMENTS 9,802,058 B2    10/2017  Zangen et al.
2003/0050527 A1*   3/2003  Fox ........................... A61N 2/02
                                                    600/13

(Continued)

FOREIGN PATENT DOCUMENTS

WO         0232504 A2    4/2002
WO      2017150490 A1    9/2017

OTHER PUBLICATIONS

Downar, et al., "New Targets for rTMS in Depression: A Review of Convergent Evidence", Brain Stimulation, SciVerse ScienceDirect, vol. 6, 2013, pp. 231-240.

(Continued)

*Primary Examiner* — Christine H Matthews
(74) *Attorney, Agent, or Firm* — Marcus S. Simon

(57) ABSTRACT

An electromagnetic coil assembly for inducing electromagnetic fields in a head region of a treated subject, the assembly comprising windings configured to define an applicatory coil portion configured for placement in close proximity to the head to induce the electromagnetic fields, and an elevated coil portion passing relatively remote from the head and configured such that electromagnetic fields thereby produced are generated substantially remote from the head, thereby allowing directing the electromagnetic fields generated by the applicatory coil portion substantially accurately to desired inner regions of the head. A support structure is used to enclose and immobilize at least a portion of the windings, while enabling elastic movement of other portions of the windings that are not held by the support structure, to thereby enable size adjustment of the coil to fit over a region of a head of the treated subject.

40 Claims, 8 Drawing Sheets

(56) References Cited

U.S. PATENT DOCUMENTS

| | | | |
|---|---|---|---|
| 2006/0094924 A1 | 5/2006 | Riehl | |
| 2009/0234243 A1 | 9/2009 | Schneider et al. | |
| 2010/0152522 A1* | 6/2010 | Roth | A61N 2/006 600/13 |
| 2014/0249352 A1 | 9/2014 | Zangen et al. | |
| 2015/0112118 A1 | 4/2015 | Mishelevich et al. | |
| 2015/0196772 A1* | 7/2015 | Ghiron | A61N 2/006 600/14 |
| 2016/0059027 A1* | 3/2016 | Zangen | A61N 2/006 600/13 |
| 2017/0326357 A1* | 11/2017 | Sacristan | A61N 2/006 |

OTHER PUBLICATIONS

George, et al., "Daily Left Prefrontal Transcranial Magnetic Stimulation Therapy for Major Depressive Disorder", Arch Gen Psychiatry, vol. 67, No. 5, May 7, 2010, 12 pages.

Johnson, et al., "Prefrontal rTMS for Treating Depression: Location and Intensity Results from the OPT-TMS Multi-Site Clinical Trial", National Institute of Health, Brain Stimulation, vol. 6, No. 2, Mar. 2013, 23 pages.

Pell, et al., "Modulation of Cortical Excitability Induced by Repetitive Transcranial Magnetic Stimulation: Influence of Timing and Geometrical Parameters and Underlying Mechanisms", Progress in Neurobiology, vol. 93, 2011, pp. 59-98.

Roth, et al., "Three-Dimensional Distribution of the Electric Field Induces in the Brain by Transcranial Magnetic Stimulation Using Fiigure-8 and Deep H-Coils", Journal of Clinical Neurophysiology, vol. 24, No. 1, Feb. 2007, pp. 31-38.

Zhang, et al., "Dysfunction of Neural Circuitry in Depressive Patients with Suicidal Behaviors: A Review of Structural and Functional Neuroimaging Studies", Progress in Neuro-Psychopharmacology & Biological Psychiatry, vol. 53, 2014, pp. 61-66.

* cited by examiner

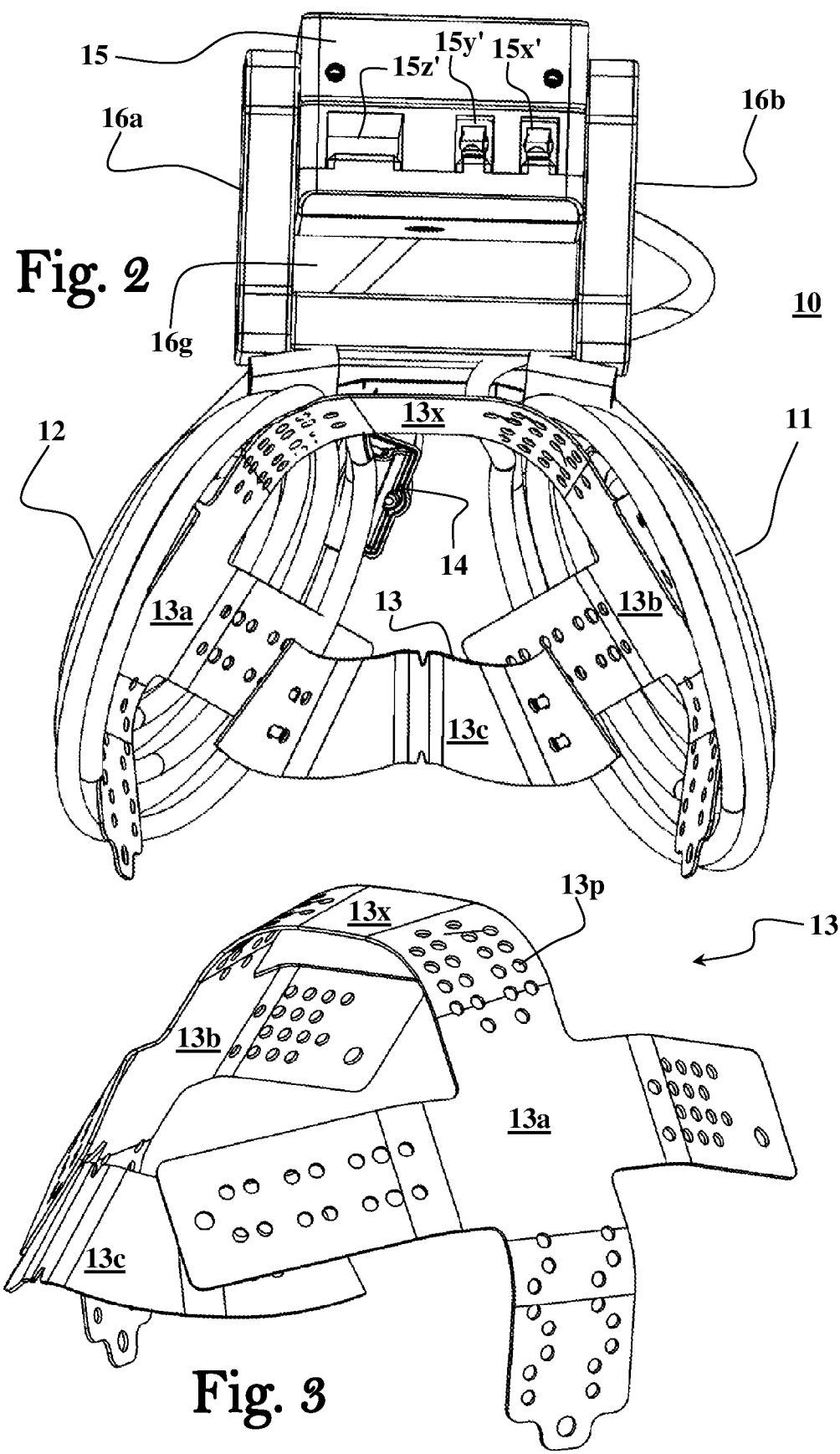

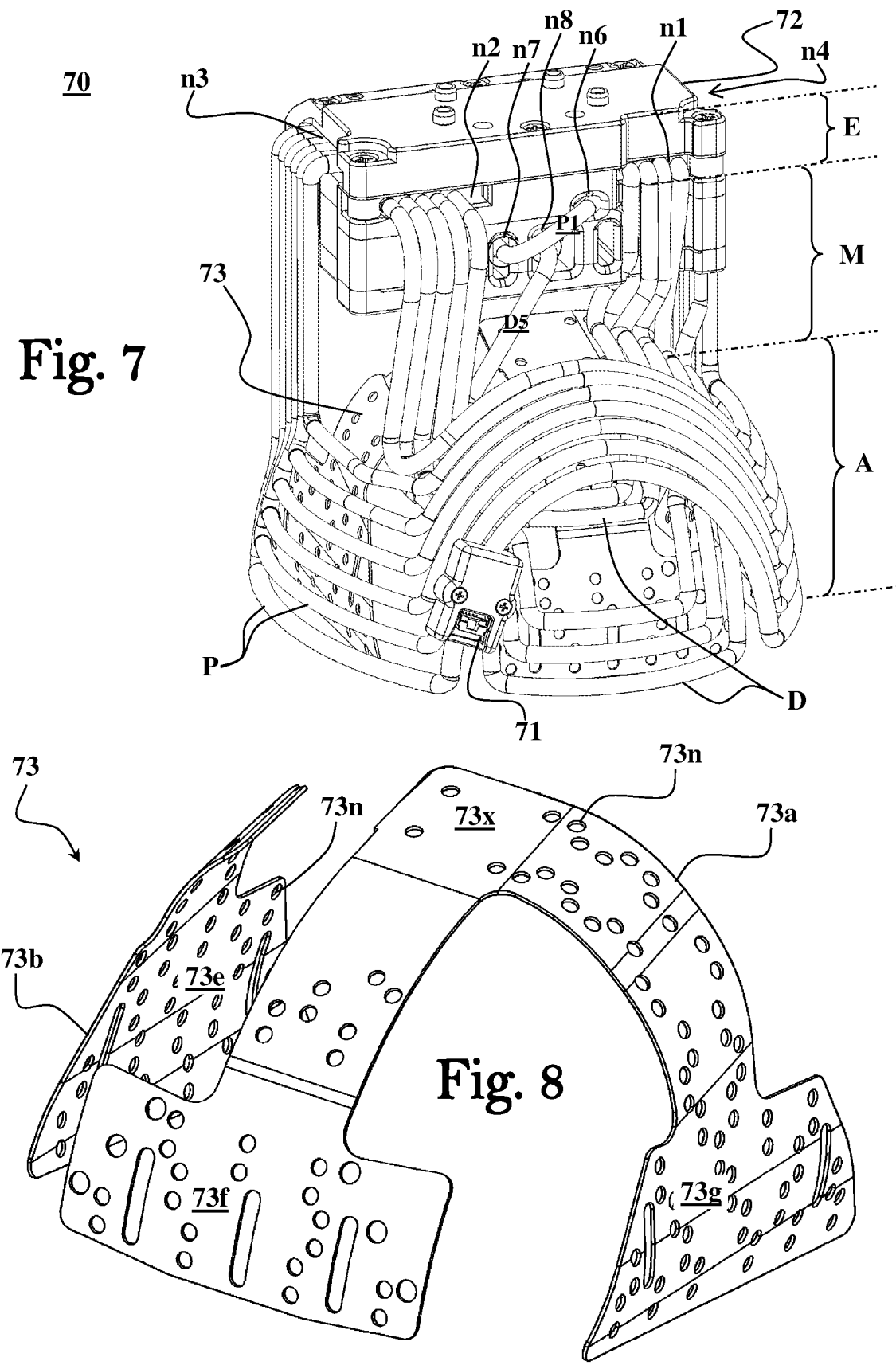

ELECTROMAGNETIC COIL ASSEMBLY

TECHNOLOGICAL FIELD

The present invention is generally in the field of electromagnetic coils, and particularly electromagnetic coils designed for placement over a head region of a hominoid.

BACKGROUND

It is known that living tissue can be stimulated by application of alternating magnetic fields produced by electromagnetic coil positioned adjacent to the tissue, to thereby induce an electric field in the living tissue. More specifically, magnetic stimulation can cause electric conduction in brain cells, and, as a consequence, generation of action potentials. For example, in transcranial magnetic stimulation (TMS) magnetic fields generated by a coil positioned on the scalp of the subject are used to induce nerve stimulation within the subject's brain.

In TMS techniques brief magnetic pulses are used to induce targeted neuronal depolarization in the brain using Faraday's law of electromagnetic induction. When TMS is carried out in a repetitive fashion, which is known as rTMS, neuroplastic long-term-potentiation-like or depression-like effects can be achieved. Conventional magnetic stimulation techniques and coils are mostly designed for superficial stimulation of the brain tissue, but typically not capable to apply deeper stimulation. The inability of superficial stimulation to induce effective stimulation in deep medial brain regions, in the ventral prefrontal cortex and other reward and mood-related brain structures, such as the nucleus accumbens (ventral striatum), yields a need for electromagnetic coil designs that can target particular areas of the brain including deep neuronal structures with minimal effect on other brain regions.

The target medial brain regions include the anterior cingulate cortex, medial prefrontal cortex, medial motor cortex, the supplementary motor area (SMA), the premotor area (PMA), medial parietal cortex, and the posterior cingulate cortex.

Stimulation of deep brain regions, generally referred to as deep TMS (dTMS), requires high intensity and accuracy which cannot be achieved by the conventional magnetic stimulators available nowadays, using standard coils configurations, without causing undesirable side effects, such as, for example, epileptic seizures or other problems associated with over-stimulation of cortical regions. In the past rTMS procedures could not directly stimulate targets greater than 2 cm beneath the surface of the skull. Deep rTMS techniques are being developed to improve the depth penetration of the electromagnetic field utilizing special coil designs, wherein multiple windings are arranged such that the electric fields thereby generated sum together, for allowing to induce direct simulation to 4 cm beneath the surface of the skull. It may be predicted that deeper brain stimulation may be more effective for the treatment of major depression and other psychiatric and neurological disorders.

Over the past decade advances in functional imaging identified specific brain areas with altered activity and volume that are associated with specific psychiatric conditions and symptoms, which can bridge over the theoretical gap between diseases of the mind-psychiatric illness, and diseases of the brain-neurological illnesses for both patients and caregivers (Downar and Daskalakis 2013; Zhang et al. 2014). Corresponding advances in bioengineering enable non-invasive modulation of those altered brain areas, via dTMS, making efficacious logical treatments widely available to psychiatric patients and reducing the stigma of mental illness as a whole.

Although deep stimulation can also be accomplished with a large circular coil or a double cone coil, their electromagnetic field decays more dramatically than with an H-coil and to reach significantly deep targets much higher intensities must be used on the surface than with an H-coil (Roth et al. 2007; Pell et al. 2011). Higher intensities can be unpleasant and potentially unsafe for the patient. H-coils stimulate wider areas than figure-8 (butterfly) coils which eliminates the need for imaging and neuro-navigation; without navigation conventional rTMS misses the target in 27-32% of patients, making conventional rTMS a costly treatment with a high number needed to treat (NNT) to reach remission (Johnson et al. 2013; George et al. 2010). The ability of H-coils to stimulate larger volumes, and deeper structures, is the reason effective therapeutic dTMS is synonymous with H-coils.

A novel approach to TMS has been previously described in International Patent Publication No. WO 02/32504, wherein deep brain stimulation is made possible while minimizing side effects. The device described therein includes a base and an extension portion, the base having individual windings for individual paths of current flow, and the extension portion designed so as to minimize unwanted stimulation of other regions of the brain.

U.S. Pat. No. 9,802,058 describes a transcranial magnetic stimulation coil which is location-specific for medial brain regions or lateral brain regions designed with multiple spaced apart stimulating elements having current flow in a first direction, and multiple return elements having current flow in a second direction which is opposite the first direction. The multiple stimulating elements are distributed around a central axis of the coil.

General Description

The present application provides electromagnetic coils assemblies designed to induce magnetic fields into tissue of a treated organ. Optionally, but in some embodiments preferably, the treated organ is a head of a treated subject. In order to effectively and efficiently stimulate deep neuronal tissue, the coil configurations disclosed herein are designed to provide high electric field magnitude in the target deep brain region (e.g., about 100 to 200 V/m), provide air passages and gaps for streaming cooling media along and/or in-between windings of the coils, and provide that high percentage of electric field is generated in deep brain regions (relative to superficial regions).

In some possible embodiments the electromagnetic coil assembly is made from an electrically conducting wire (e.g., made of Copper) having cross-sectional area of about 7 to 10 mm$^2$ and a length of about 500 to 800 cm, wound to form a coil comprising a plurality of windings (also referred to herein as loops) electrically connected in series. The inductance of the electromagnetic coil assembly can generally be in a range of 13 to 20 µH, and their electrical resistance can be generally be in a range of 0.01 to 0.04 Ohm. The disclosed coils are configured to generate magnetic field in a range of 0.05 to 2 Tesla deep inside the subject's head, and establish an electric field of about 100 to 200 V/m at a distance of about 0.5 to 3 cm from the windings of the applicatory coil portions.

The plurality of windings can be held by a support structure configured to enclose and immobilize at least a portion of each winding of the coil assembly, while enabling elastic movement of other portions of the windings, that are not held by the support structure and configured to fit over head portions of the treated subject. In this way the size of the coil assembly can be readily adjusted to fit over a region of a head of a treated subject. The coil assembly comprises an applicatory coil portion configured for placement in close proximity to the head of the treated subject and induce electromagnetic fields thereinto, and an elevated coil portion passing relatively remote from the subject's head and configured such that electromagnetic fields produced by currents (e.g., return currents) passing therethrough are generated substantially remote from the subject's head to prevent them from interfering with the electromagnetic fields generated by the applicatory coil portions of the coil, thereby allowing directing the electromagnetic fields generated by the wires in the applicatory coil portions substantially accurately to specifically desired regions of the treated subject's head.

The support structure can be configured to form an air gap between the applicatory and remote coil portions of the coil assembly for streaming cooling media (e.g., fluid/gas) along and/or in-between windings of the applicatory coil portions of the coil assembly. The coil assembly can be arranged inside a helmet. The helmet can be connected by an adaptor to a positioning device. The helmet can be connected to a cable for passing electric currents generated by a signal generator, such as, but not limited to, a neurostimulator, through the windings/loops of the electromagnetic coil. The helmet can be accordingly configured to circulate the cooling media along and/or in-between the windings/loops of the coil assembly for cooling them during their operation. One or more temperature sensors can be coupled to applicatory coil portion(s) of the coil assembly and configured to generate measurement signals/data indicative of the temperature of the coil windings. A control unit can be used to regulate the cooling media streamed through the air gap for cooling the coil windings, and/or to regulate the electric current supplied to the windings of the coil during operation.

Some of the electromagnetic coils disclosed herein are types of H-coils in a form of a butterfly-shaped coil designed to induce activation of brain structures in the medial prefrontal cortex (PFC) including the anterior cingulate cortex (ACC), associated with cognitive behavior and executive function (differentiation abilities, goal-oriented cognition, and social "control"), and motor cortex areas. The electromagnetic coils designs can be thus used, inter alia, in treatment of obsessive compulsive disorder (OCD), post-traumatic stress disorder (PTSD), major depressive disorder (MDD), migraine, blepharospasm, Tourette's syndrome, post-stroke rehabilitation, chronic pain and cocaine addiction.

In some possible embodiments the butterfly-shaped electromagnetic coil is made from an electrically conducting wire (e.g., made of Copper) having cross-sectional area of about 7 to 10 mm$^2$ and a length of about 500 to 700 cm, wound to form a coil having two spaced apart circular wings/lobes electrically connected in series, each wing/lobe comprising a plurality of windings (also referred to herein as loops) spiraling outwardly from one or more innermost windings towards one or more outermost windings. The distance between the wound wings/lobes is selected so as to increase the depth of penetration of the induced electromagnetic field into the treated tissue.

Optionally, and in some embodiments preferably, the wound wings/lobes of the electromagnetic coil are electrically connected by a wire segment electrically connecting an innermost winding/loop of one wound wing/lobe to an outermost winding/loop of the other wound wing/lobe. The spiraling directions of the windings of the coil are made in some embodiments in opposite directions. For example, and without being limiting, the windings of a first wing/lobe can spiral in a clockwise direction from the inner most winding/loop to the outermost winding/loop, and the windings of a second wing/lobe can spiral in a counterclockwise direction from the inner most winding/loop to the outermost winding/loop. This way, by connecting an outermost winding/loop of the first wing/lobe of the coil to an innermost winding/loop of the second wing/lobe of the coil, similar magnetic flux directions can be applied by the wings/lobes central segments, which are close to the coil central axis, and additive electromagnetic field is induced under the coil central region.

In some embodiments each wing/lobe comprises eight windings/loops. The windings/loops can be arranged in each wound wing/lobe in groups, where the windings/loops in each group are concentric and having substantially the same diameter. For example, in some embodiments each wound wing/lobe comprises one or more pairs of concentric windings/loops having substantially the same diameter. In case each wound wing/lobe comprises eight windings/loops, four concentric serially connected wire rings are formed in each wound wing/lobe, where each wire ring comprises a pair of concentric windings/loops having substantially the same diameter.

The diameter of the innermost windings/loops in the wound wings/lobes can be about 7 to 7.5 cm in some embodiments, and the diameter of outermost windings/loops can be about 12 to 14 cm in some embodiments. The spacing between adjacent groups/rings of concentric windings/loops having the substantially same diameter can be about 0.3 to 1 cm in some embodiments, for efficiently cooling them during operation by streaming a cooling gas/fluid therealong and/or therethrough.

In some embodiments the windings/loops in at least some of the groups/rings of concentric windings/loops have an elliptic shape. The major and minor axes of the innermost windings/loops in the wound wings/lobes can be in some possible embodiments about 6.5 to 7.5 cm and 7.5 to 9 cm, respectively, and the major and minor axes of outermost windings/loops can be in some possible embodiments about 11 to 13 cm and to 13 to 15 cm, respectively.

The windings/loops of the electromagnetic coil can be gradually elevated in each wound wing/lobe in a descending order with respect to the average diameter of each group/ring of concentric windings/loops, to thereby form two domed-shaped (conical) wound wing/lobe structures connected by the wire segment communicating between an innermost winding/loop in one wing/lobe and an outermost winding/loop of the other wing/lobe. The support structure comprises in some embodiments a fastening/reinforcing structure used to hold the wound wings/lobes in tilted conformation of one wing/lobe with respect to the other (e.g., with an angle of about 120° to 140° between the wings/lobes), thereby defining a semi-spherical volume between the wound wings/lobes suitable for fitting the coil assembly over the head of the treated subject. The fastening/reinforcing structure is thereby configured to enable limited elastic movement of the wound wings/lobes, and thereby permit adjusting the semi-sphere volume defined between the wound wings/lobes to fit over a head region of a treated subject.

The inductance of the butterfly-shaped electromagnetic coil can be in some embodiments in a range of 13 to 14 µH, preferably about 13.2 µH, and its electrical resistance can be in a range of 0.015 to 0.035 Ohm, preferably about 0.025 Ohm. With such coil assembly a magnetic field in a range of 0.05 to 0.6 Tesla can be achieved deep inside the subject's head, and an electric field of about 100 V/m can be achieved at a distance of about 3 cm from the wound lobes of the electromagnetic coil. The one or more temperature sensors can be coupled to one or more of the winding of the electromagnetic coil assembly, and one or more respective wires can be used to communicate signals generated by the temperature sensors to external devices (e.g., control unit) over the cable connected to the helmet.

In some embodiments a free wire end extends from each wound wing/lobe towards respective connectors located in a wiring assembly mounted above and relatively remote (about 5 to 8 cm) from the applicatory portions of wound wings/lobes, thereby forming the air gap between the wound lobes and the wiring assembly for streaming the cooling media Some of the electromagnetic coil assemblies disclosed herein are in a form of electromagnetic H-coil assemblies designed to induce electromagnetic fields into a head of a treated subject. H-Coils are a unique and innovative technology which enables direct non-invasive activation of deep brain structures. In order to stimulate effectively deep neuronal tissue, the H-coil configurations disclosed herein are designed to provide high electric field magnitude in the target deep brain region (e.g., about 100 V/m), and provide that high percentage of electric field is generated in the deep target region relative to superficial regions.

The H-coils disclosed herein can be used to induce activation of brain structures related to the reward system, which is considered to play a significant role in the occurrence of clinical depression. The reward system includes neuronal structures in the cortical and sub-cortical prefrontal cortex (PFC), both dorso-lateral PFC, ventro-lateral PFC, and medial PFC. Accumulating evidences indicate that interactions between regions in the PFC, and both the ventral tegmental area (VTA) and the nucleus accumbens, have a significant role in sequences related to the reward system, including depression. The H-coil embodiments of the present application can induce effective activation of cortical and sub-cortical PFC regions, both lateral and medial, with a preference for the left hemisphere.

In some possible embodiments the H-coil is made from an electrically conducting wire (e.g., made of Copper) having cross-sectional area of about 7 to 10 mm$^2$ and a length of about 700 to 800 cm, winded to form 12 windings (also referred to herein as loops). The windings/loops of the electromagnetic coil are electrically connected in series. Each winding/loop have an applicatory portion configured for placement in close proximity to the head of the treated subject and induce electromagnetic field thereinto, an elevated portion passing in a transverse (horizontal) plane remote from the head of the treated subject, and one or more intermediate portions electrically connecting the applicatory portion of the loop to its elevated portion.

Optionally, and in some embodiments preferably, the electromagnetic coil is designed for TMS applications. Particularly, embodiments of the coil assemblies disclosed herein are configured for effective activation of cortical and sub-cortical prefrontal and orbitofrontal neuronal structures, with a preference to the left hemisphere. Thus, in some embodiments, the coil assembly is configured to induce electromagnetic fields in anterior-posterior axis directions in lateral prefrontal regions, and lateral-medial axis direction in medial frontal regions, of the subject's brain.

The applicatory portions of the windings/loops of the electromagnetic coil, also referred to herein as the effective part of the coil, form a conductive wire structure having a helmet (half-donut)-like shape, designed for placement over the head of the treated subject. The inner rim of the effective part of the electromagnetic coil can be made flexible in order for it to fit over a region of a head of the treated subject. The H-coil is contained in some embodiments inside a helmet, which can be connected by an adaptor to a positioning device. The helmet can be connected to a cable for passing electric currents generated by a signal generator, such as, but not limited to, a neurostimulator, through the windings/loops of the electromagnetic coil.

The inductance of the electromagnetic H-coil can be in some embodiments in a range of 19.4 to 19.6 µH, preferably about 19.5 µH, and its electrical resistance in a range of 0.01 to 0.02 Ohm, preferably about 0.015 Ohm. The distance between adjacently located wires in the applicatory/effective part of the coil assembly can be generally about 1 cm. With such coil assembly an electric field of about 200 V/m can be achieved at a distance of about 0.5 cm from the applicatory portions of the windings/loops of the electromagnetic coil. Temperature sensors can be coupled to one or more of the winding/coils of the electromagnetic coil for measuring the temperature of the coil windings. One or more respective wires can be used to communicate signals generated by the temperature sensors to external devices (e.g., control unit) over the cable connected to the helmet.

In some embodiments the coil assembly comprises one or more medial loops the applicatory portion of which configured to traverse a top medial region of the treated subject's head, and one or more peripheral loops the applicatory portion of which configured to traverse a peripheral region of the treated subject's head, and thereby at least partially cross a portion of the medial loops. Some portions of the peripheral and medial loops can be oriented along the anterior-posterior axis on the left hemisphere, to thereby stimulate neuronal pathways along this axis. Other portions of the peripheral loops can be similarly placed over the right hemisphere. The portions of the peripheral loops crossing the medial loops can be placed directly above wire portions of the medial loops to produce electric field along the lateral-medial axis, in prefrontal and orbitofrontal regions (when placed over the frontal cortex).

In some embodiments the coil assembly comprises seven peripheral windings/loops and five medial windings/loops. The inner rim of the coil assembly is configured to locate 12 wire segments in the applicatory portions of the peripheral and medial windings/loops over the left hemisphere of the subject's head, each having a length in a range of 7 to 12 cm, and a separation distance of about 1 cm between adjacently located wires for streaming the cooling media therealong and/or therebetween.

In some possible embodiments the medial windings/loops comprise one or more upper-medial loops, the applicatory portion of which is configured to traverse an upper-medial region of subject's head, and one or more lower-medial loops, the applicatory portion of which configured to traverse a lower-medial region of subject's head. Wire segments in the applicatory portions of the upper and lower medial windings/loops can be configured as part of the inner rim of the coil assembly that pass over the left hemisphere of the subject's head.

Optionally, and in some embodiments preferably, the coil assembly comprises two upper-medial windings/loops, three lower-medial loops, and seven peripheral loops. In this configuration three wire segments of the lower-medial loops extend towards the forehead of the subject's head, and their continuations pass in the left-right direction along the orbitofrontal cortex, with separation of about 1 cm between them. In this coil assembly design six wire segments in the applicatory portions of the peripheral loops can be passed over the right hemisphere. The distance between adjacently located wire segments of the peripheral loops passing over the right hemisphere can be about 0.8 cm.

In some embodiments the elevated portions of the winding/loops are located at a distance of about 6 to 8 cm from their applicatory portions, in order to form a wide air passage therebetween. The intermediate portions of the windings/loops can be parallel to each other and pass along lateral parallel planes, substantially parallel to a sagittal plane of the treated subject, with a distance of about 0.3 cm between adjacently located wires. In this way electromagnetic fields produced by currents (e.g., return currents) passing through the intermediate and elevated portions of the loops, are generated substantially remote from the subject's head and thereby prevent them from interfering with the electromagnetic field generated by the applicatory portions of the loops.

The helmet comprising the coil assembly is configured in some embodiments to circulate the cooling media (fluid or gas coolant) along and/or in-between windings/loops of the coil assembly. Thus, the distance provided between the applicatory and elevated portions of the windings/loops can be exploited for streaming the coolant along and/or in-between the windings/loops, and thereby permit effective control of their temperatures to guarantee that the temperature of the winding of the coil is maintained within a desired operational temperature range (e.g., about 16° C. to 25° C.), and to prevent overheating.

Optionally, and in some embodiments preferably, the elevated portions of the peripheral loops laterally pass (from one side to the other—left-to-right or wise versa) one parallel to the other in a first transverse plane, and the elevated portions of the medial loops pass in a second transverse plane in a form of interfolding arc patterns, in order to achieve simplicity of design and structural stability.

One inventive aspect of the subject matter disclosed herein refers to an electromagnetic coil for inducing electromagnetic fields in a head region of a treated subject. The coil assembly comprising a plurality of windings configured to define an applicatory coil portion configured for placement in close proximity to the head of the treated subject to induce the electromagnetic fields, and an elevated coil portion passing relatively remote from the head of the treated subject and configured such that electromagnetic fields thereby produced are generated substantially remote from the head of the treated subject to prevent them from interfering with the electromagnetic fields generated by the applicatory portion of the coil, thereby allowing directing the electromagnetic fields generated by the applicatory coil portion substantially accurately to desired inner regions of the head of the treated subject. The coil assembly comprises a support structure configured to enclose and immobilize at least portion of windings of the coil, while enabling elastic movement of other portions of the windings that are not held by the support structure, to thereby enable size adjustment of the coil to fit over a region of a head of the treated subject. This way an air gap is formed with the support structure used to maintain an open passage between the applicatory and remote coil portions for streaming cooling media along or in-between windings of the applicatory coil portions.

The electromagnetic coil assembly is made in some embodiments from a wire having cross-sectional area of about 7 to 10 mm$^2$, a length of about 500 to 800 cm, and a total electrical resistance of about 0.01 to 0.04 Ohm. Inductance of the plurality of windings of the coil can be about 13 to 20 µH. Optionally, but in some embodiments preferably, the windings of the applicatory coil portion are configured to generate magnetic field in a range of 0.05 to 1.5 Tesla inside the head of the treated subject, and establish an electric field of about 100 to 200 V/m at a distance of about 0.5 to 3 cm from the windings of the electromagnetic coils.

The coil assembly comprises in some embodiments two domed-shaped coil structures made of two spaced apart wound wings/lobes serially connected by an intermediate wire and configured to define a semi-spherical volume for fitting over a head region of a treated subject, and the support structure is attached to superior sections of the dome-shaped coils to thereby permit elastic movement of the wound wings/lobes in sideway directions. The support structure can comprise a wiring assembly located above and relatively remote to the dome-shaped coils and configured to receive and hold the elevated coil portion, to thereby define the air gap between the elevated coil portion and the applicatory coil portion i.e., the dome-shaped coils. The air gaps are configured for directing a stream of cooling media therethrough for cooling the coil assembly and prevent overheating. In some embodiments the coil assembly is configured for mounting inside a helmet structure while maintaining the certain degree of elastic movement of the wound wings/lobes.

Optionally, and in some embodiments preferably, the coil assembly comprises one or more temperature sensors coupled to at least one of the dome-shaped coils. At least one temperature sensor can be placed in areas that absorb heat substantially produced by the two wound lobes. The one or more temperature sensors can be attached to wire segment(s) of one of the wound lobes in a region located adjacent to the wire segments of the other wound lobe.

Each of the dome-shaped coils can comprise an innermost loop, an outermost loop, and at least one wire segment spiraling between the innermost and outermost loops. In some embodiment the intermediate wire is configured to connect between an innermost loop in one of the dome-shaped coils and an outermost wire in the other dome-shaped coil. The spiraling wire segment of the dome-shaped coils is spiraling in possible embodiments in opposite directions. A diameter of the innermost loop can be in a range of 7 to 7.5 cm. A diameter of the outermost loop can be in a range of 12 to 14 cm.

Optionally, but in some embodiments preferably, the windings/loops of the dome-shaped coils have an elliptic shape. The major and minor axes of the innermost windings/loops in the wound wings/lobes can be in some possible embodiments about 6.5 to 7.5 cm and 7.5 to 9 cm, respectively, and the major and minor axes of the outermost windings/loops can be in some possible embodiments about 11 to 13 and to 13 to 15 cm, respectively.

Optionally, and in some embodiments preferably, each dome-shaped coil comprises groups of concentric loops, each group of concentric loop can comprise two or more concentric windings having substantially a same diameter, or two or more concentric elliptic loops, each concentric elliptic loop comprising two or more concentric windings having substantially same major and minor axes. Spacing between adjacently located groups of concentric loops is selected in some embodiments to be in a range of 0.3 to 1 cm.

In some embodiments the support structure comprises a fastening structure configured to hold and immobilize the superior sections of the dome-shaped coils and enforce a tilted conformation of the wound lobes one with respect to the other. The fastening structure can be configured to maintain an angle of about 120° to 140° between the wound coils. The fastening structure optionally comprises a base portion and two laterally extending wings portions. The wing portions configured to attach to the superior sections of the wound lobes and being tilted with respect the base section to reinforce the angle obtained between the wound lobes. A channel may be formed in the fastening structure for receiving and holding the intermediate wire therein.

Optionally, a distance between the dome-shaped coils is in a range 2 to 7 cm. In some embodiments a distance between superior sections of the wound lobes is in a range of 1.5 to 5 cm, optionally about 1.5 to 2.5 cm. A distance between inferior sections of the dome-shaped coils can be in a range of 16 to 18 cm. Optionally, and in some embodiment preferably, a cross-sectional area of the coil wires is in a range of 7 to 10 mm$^2$.

The support structure may comprise one or more support members configured to attach the wiring assembly to the fastening structure and maintain the air gap therebetween. In some embodiments the one or more support members have a slanted structure configured for mounting the wiring assembly posterior to the wound lobes for preventing electromagnetic fields interferences.

The coil assembly comprises in some embodiments a plurality of loops, each loop having an applicatory portion configured for placement in close proximity to a head region of a treated subject and induce electromagnetic fields thereinto, an elevated portion passing in a transverse (horizontal) plane remote from the applicatory portion and from the subject's head, and intermediate portions electrically connecting the applicatory portion to the elevated portion. In some embodiments the coil assembly comprises one or more medial loops the applicatory portion of which configured to traverse a medial region of the subject's head, one or more peripheral loops the applicatory portion of which configured to traverse a peripheral region of the subject's head and thereby at least partially cross a portion of the medial loops, and the support structure configured to hold and immobilize the elevated portion of the peripheral loops in a first transverse plane and the elevated portions of the medial loops in a second transverse plane substantially parallel to the first transverse plane, while permitting elastic movement in the intermediate and applicatory portions of the loops. Optionally, and in some embodiments preferably, the first transverse plane is located above and adjacent the second transverse plane. The remote portions of the peripheral loops can pass in the first transverse plane substantially parallel to a frontal plane of the subject. The peripheral and medial loops are configured in some embodiments for mounting inside a helmet while maintaining the elastic movement in the intermediate and applicatory portions of the loops.

The at least one temperature sensor can be attached or thermally coupled to wire segment(s) in an applicatory portion of at least one of the loops. In possible embodiments the at least one temperature sensor is coupled to wire segment(s) in the applicatory portion of one or more peripheral loops in a region that at least partially crosses a portion of the medial loops.

Optionally, and in some embodiments preferably, the elevated portion of each of the medial loops is arc-shaped, thereby affecting different orientations of the elevated peripheral and medial loop portions. The one or more medial loops can comprise one or more upper-medial loops the applicatory portion of which configured to traverse an upper-medial region of the subject's head, and one or more lower-medial loops the applicatory portion of which configured to traverse a lower-medial region of the subject's head. This way the arc-shaped elevated portions of the upper-medial loops can be at least partially accommodated in the arc-shaped elevated portion of the lower-medial loops. The support structure can comprise a fastening structure comprising two lateral openings connected by an elongated channel configured to accommodate the elevated portions of the peripheral loops. The fastening structure can comprise two frontal openings connected by a plurality of arc-shaped channels passing below the elongated channel and configured to accommodate the remote portions of the upper-medial and lower-medial loops.

In some embodiments the wire segments in the applicatory portions of the periphery loops, the lower-medial loops, and the upper-medial loops are configured to pass over one lateral side area of the subject's head. A semi-spherical structure can be obtained by placing the loops one above the other in a descending order with respect to an average diameter defined by each loop. The wire segments that pass over the one lateral side area of the subject's head can be thus arranged such that the wire segments of the peripheral loops are located below the wire segments of the lower-medial loops, and the wire segments of the lower-medial loops are located below the wire segments of the upper-medial loops. The coil assembly comprises in some embodiments seven peripheral loops. Optionally, and in some embodiments preferably, the coil assembly comprises two upper-medial loops.

Properties of the H-coil assembly may include at least one of the following features: cross sectional area of the wires of the loops is in the range of 7 to 10 mm$^2$; the peripheral and medial loops are made from a continuous wire having a length in a range of 700 to 800 cm; the loops are configured to generate magnetic field in a range of 0.4 to 3.2 Tesla deep inside the subject's head; inductance of the coil is in a range of 19.4 to 19.6 µH; electrical resistance of the coil is in a range of 0.01 to 0.02 Ohm; and/or applicatory portions of the loops configured to induce an electric field of about 200 V/m.

Another inventive aspect of the subject matter disclosed herein relates to a helmet for application of transcranial magnetic stimulations, the helmet comprising: a wearable housing; an electromagnetic coil assembly enclosed inside the housing and comprising a plurality of coil windings configured to define an applicatory coil portion configured to fit over a portion of a head of a treated subject and induce electromagnetic fields thereinto, and an elevated coil portion passing relatively remote to the head of the treated subject and configured such that electromagnetic fields thereby produced are generated substantially remote from the head of the treated subject to prevent them from interfering with the electromagnetic fields generated by the applicatory portion of the coil, thereby allowing directing the electromagnetic fields generated by the applicatory coil portion substantially accurately to desired inner regions of the head of the treated subject; a support structure configured to enclose and immobilize at least a portion of each winding of the coil to thereby permit elastic movement of other portions of the windings, that are not held by the support structure inside the housing, to thereby enable size adjustment of the coil to fit over a region of a head of the treated subject.

The support structure configured to define an air gap between the applicatory and remote coil portions of the windings of the coil assembly for streaming cooling media along and/or in-between applicatory coil portions of the windings; and at least one air inlet configured for receiving a flow of the cooling media and stream it through the air gap into the helmet. The helmet can be configured to circulate the cooling media along and/or in-between the windings/ loops of the coil assembly for cooling them during their operation. One or more temperature sensors can be coupled to applicatory portion(s) of the coils (e.g., to areas that absorb heat produced by the windings of the coil) and configured to generate measurement signals/data indicative of the temperature of the coil windings.

In some embodiments the windings form two serially connected dome-shaped coils configured to fit over a head region of a treated subject. The support structure can be attached to superior sections of the dome-shaped coils, thereby forming a butterfly-shaped structure configured to permit elastic movement of the wings (the dome-shaped coils) inside the housing. Optionally, but in some embodiments preferably, the support structure is configured to define the air gap above the dome-shaped coils.

The one or more temperature sensors can be coupled to one or more wires of one of the dome-shaped coils in areas that absorb heat substantially produced by the two dome-shaped coils. Optionally, and in some embodiments preferably, the one or more temperature sensors are attached to wire segment(s) of one of the dome-shaped coils in a region located adjacent to wire segments of the other dome-shaped coils.

In some embodiments each of the dome-shaped coils comprises an innermost loop, an outermost loop, and at least one wire segment spiraling between the innermost and outermost loops. An intermediate wire can be used for connecting between the dome-shaped coils. The intermediate wire can be configured to connect between an innermost loop in one of the dome-shaped coils and an outermost wire in the other dome-shaped coil. A diameter of the innermost loop can be selected to be in a range of 7 to 7.5 cm. A diameter of the outermost loop can be in a range of 12 to 14 cm. Optionally, but in some embodiments preferably, the windings/loops of the dome-shaped coils have an elliptic shape with major and minor axes of the innermost windings/ loops in the wound wings/lobes of about 6.5 to 7.5 cm and 7.5 to 9 cm, respectively, and the major and minor axes of the outermost windings/loops of about 11 to 13 and 13 to 15 cm, respectively.

Each dome-shaped coil comprises in some embodiments groups of concentric loops, each loop comprising two or more concentric windings having substantially a same diameter. Optionally, a spacing between adjacently located groups of concentric loops is in a range of 0.3 to 1 cm.

The support structure comprises in some embodiments a fastening structure configured to hold and immobilize superior sections of the dome-shaped coils and enforce a tilted conformation of the coils one with respect to the other. The fastening structure can be configured to maintain an angle of about 120° to 140° between the dome-shaped coils.

In some embodiments the fastening structure comprises a base portion and two laterally extending wings portions, the wing portions configured to attach to superior sections of the dome-shaped coils and being tilted with respect the base section to reinforce the angle between the dome-shaped coils.

A distance between superior sections of the domed-shaped coils can be set to be in a range of 2 to 5 cm. A distance between inferior sections of the domed-shaped coils is optionally in a range of 16 to 18 cm.

The support structure comprises in some embodiments one or more support members configured to attach a wiring assembly to the fastening structure and maintain the air gap therebetween. The one or more support members can have a slanted structure configured for mounting the wiring assembly posterior to the wound dome-shaped coils.

In some possible embodiments the electromagnetic coil assembly comprises an applicatory portion configured for placement in close proximity to head of a treated subject and induce electromagnetic fields thereinto, an elevated portion passing in a transverse plane remote from the head of the treated subject, and an intermediate portion electrically connecting between the applicatory and elevated portions while maintaining a predefined gap therebetween. One or more reinforcing elements can be used to hold and immobilize the elevated portion of the coil inside the housing of the helmet. The electromagnetic coil assembly may comprise one or more medial loops the applicatory portion of which configured to traverse a medial region of the head of the treated subject, and one or more peripheral loops the applicatory portion of which configured to traverse a peripheral region of the head of treated subject and thereby at least partially cross a portion of the medial loops. The one or more reinforcing elements can be configured to hold the elevated portions of the peripheral loops in a first transverse plane and the elevated portions of the medial loops in a second transverse plane substantially parallel to the first transverse plane, while permitting elastic movement of the intermediate and applicatory portions of the loops inside the housing.

A yet another inventive aspect disclosed herein relates to a brain stimulation system comprising the helmet for application of transcranial magnetic stimulations described hereinabove or hereinbelow, a signal generator configured to drive the coil assembly of the helmet for inducing electromagnetic fields inside the subject's head, an electric pump configured to stream a coolant to the coil assembly, a sensor device configured to measure at least one property or condition associated with the operational coil portion and generate measurement data indicative thereof, and a control unit configured and operable to generate signals for operating the pump and the signal generator at least partially based on said measurement data. The brain stimulation system can comprise one or more sensor elements attached to the subject's head for measuring electrical activity of the subject's brain and generating measured brainwaves data indicative thereof. The control unit can be configured and operable to process the brainwaves data and generate based thereon control signals for adjusting the activation signals generated by the signal generator.

BRIEF DESCRIPTION OF THE DRAWINGS

In order to understand the invention and to see how it may be carried out in practice, embodiments will now be described, by way of non-limiting example only, with reference to the accompanying drawings. Features shown in the drawings are meant to be illustrative of only some embodiments of the invention, unless otherwise implicitly indicated. In the drawings like reference numerals are used to indicate corresponding parts, and in which:

FIG. 2 schematically illustrates a back view of the butterfly-shaped electromagnetic H-coil assembly;

FIG. 3 schematically illustrates a head shield of the butterfly-shaped H-coil assembly of some possible embodiments;

FIG. 8 schematically illustrates a head shield of the H-coil assembly of some possible embodiments;

DETAILED DESCRIPTION OF EMBODIMENTS

Figure 1:
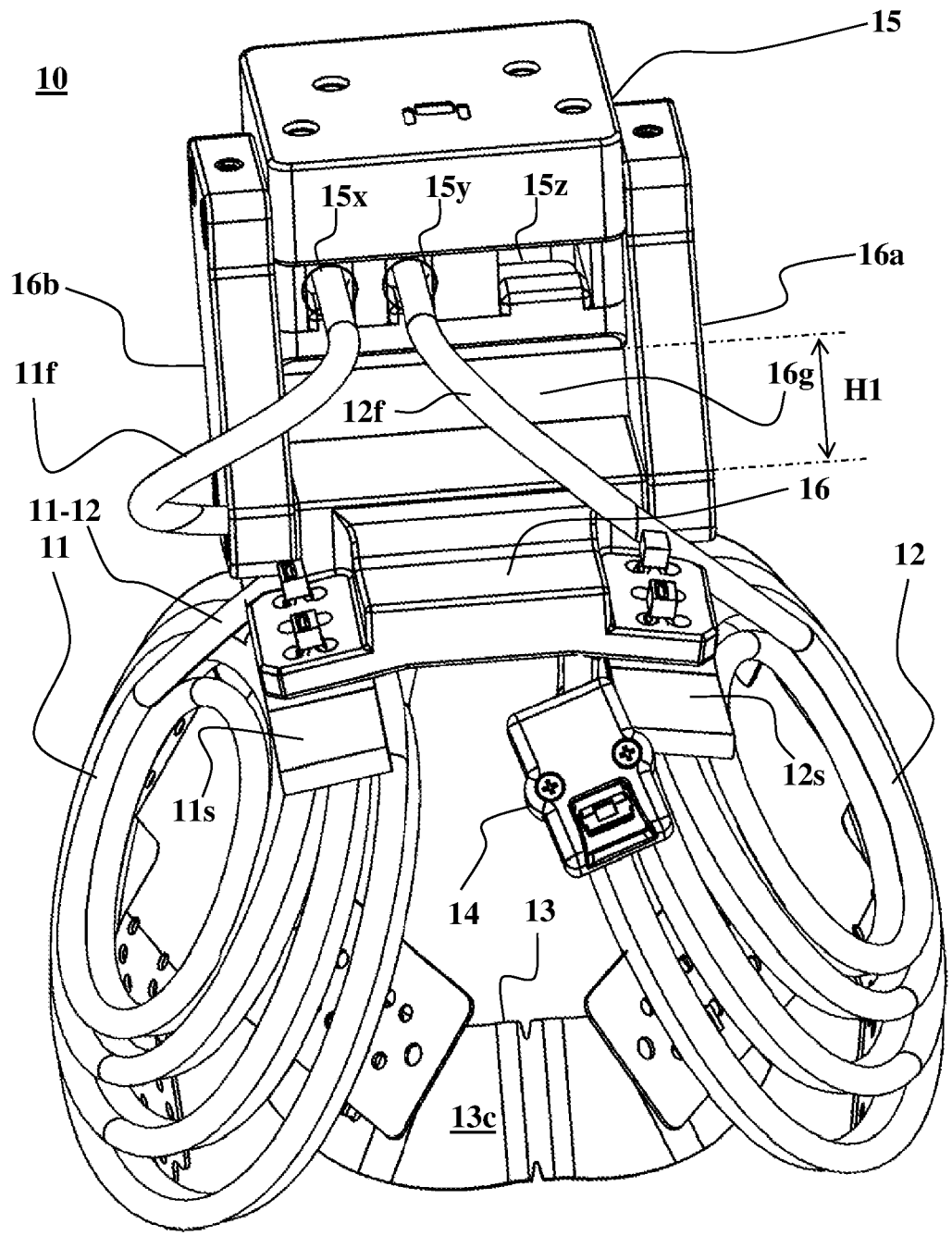
FIG. 1 schematically illustrates a front perspective view of a butterfly-shaped electromagnetic H-coil assembly according to some possible embodiments.

One or more specific embodiments of the present disclosure will be described below with reference to the drawings, which are to be considered in all aspects as illustrative only and not restrictive in any manner. In an effort to provide a concise description of these embodiments, not all features of an actual implementation are described in the specification. Elements illustrated in the drawings are not necessarily to scale, or in correct proportional relationships, which are not critical. Emphasis instead being placed upon clearly illustrating the principles of the invention such that persons skilled in the art will be able to make and use the disclosed coil assemblies, once they understand the principles disclosed herein. This invention may be provided in other specific forms and embodiments without departing from the essential characteristics described herein.

Some embodiments of the present application provide butterfly-shaped electromagnetic coils that can be effectively used to apply deep transcranial magnetic stimulation (dTMS) for treating various mental/psychological and/or physiological/neuropsychiatric disorders. The availability of this technology is dramatically changing the practice of psychiatry and neurology, as well as the perception of mental illness. For example, and without being limiting, the butterfly-shaped coils assemblies disclosed herein can be used for the treatment of obsessive compulsive disorders, posttraumatic stress disorders, migraine, blepharospasm, Tourette's syndrome, and cocaine addiction.

FIG. 1 shows a top perspective view of a butterfly-shaped electromagnetic coil assembly 10 according to some possible embodiments. The electromagnetic butterfly-shaped coil assembly 10 comprises two spaced apart wings/lobes of windings/loops, 11 and 12, forming two domed-shaped coil structures, a shield element 13 attached to bottom inner side portions of the coils structure, and a support structure comprising a fastening structure 16 connecting between superior sections of the two spaced apart wings/lobes of windings/loops 11 and 12. The fastening structure 16 comprises a wiring assembly 15 mounted above and relatively remote to the applicatory portions of the coils and configured to receive elevated portions of the coils, thereby forming an air gap 16g therebetween. One or more buffering straps 11s and 12s can be attached between the fastening structure 16 and the superior sections of the lobes 11 and 12, for holding straps for attachment of the coil to the head of the treated subject.

One or more temperature sensors 14 coupled to one or more wire segments in one of the wings/lobes of windings/loops 11 and 12 can be used to implement temperature control mechanism configured to maintain the temperature of the windings within a desired operational temperature range and prevent overheating. The one or more temperature sensors 14 can be placed in areas of the electromagnetic coil that absorb heat produced by the two wings/lobes of windings/loops 11 and 12. In this specific and non-limiting example a single temperature sensor 14 is attached to wire segment(s) in the right-side wing/lobe 12 located adjacent to wire segments in the left-side wing/lobe 11.

Optionally, and in some embodiments preferably, the domed-shaped coil structures are made from a single continuous wire turned to form the two lateral wound wings/lobes 11 and 12 electrically connected in series by an intermediate wire segment 11-12. Each of the wound lobes 11 and 12 comprises a plurality of circular windings/loops spiraling outwardly from one or more innermost windings towards one more outermost windings. In some embodiments the intermediate wire segment 11-12 connects an innermost winding/loop of one of wings/lobes to an outermost winding/loop of the other lobe.

A free end remote portion 11f of the wire extends from the wound wing/lobe 11 to the wiring assembly 15, and introduced via the opening 15x into the wiring assembly for attachment to a terminal connector (C1 in FIGS. 4 and 6) mounted thereinside. A free end remote portion 12f of the wire extends from the wound wing/lobe 12 to the wiring assembly 15, and introduced via the opening 15y into the wiring assembly 15 for attachment to a terminal connector (C2 in FIGS. 4 and 6) mounted thereinside. In this specific and non-limiting example the free end remote portion 12f extends from an innermost winding/loop in the right-side wing/lobe 12, the intermediate wire segment 11-12 connects an outermost winding/loop of the right-side wing/lobe 12 to an innermost winding/loop of the left-side lobe 11, and free end remote portion 11f extends from an outermost winding/loop in the left-side wing/lobe 11.

The Windings/loops in each wound wing/lobe 11 and 12 are gradually elevated with respect to windings/loops adjacently located thereto in the wing/lobe in a descending order with respect to the diameter of the windings/loops, to thereby form two domed-shaped (conical) spiral coil structures connected by the intermediate wire segment communicating between an innermost winding/loop in one wing/lobe and an outermost winding/loop of the other wing/lobe. The fastening structure 16 and the shield element 13 are configured in some embodiments to hold the wound wings/lobes in tilted conformation in some predefined angle (e.g., about 130°) therebetween, thereby defining a semi-spherical volume between the wings/lobes 11 and 12 suitable for fitting the coil assembly over a head region of the treated subject. This configuration of the coil assembly 10 permits the wound wings/lobes 11 and 12 some degree of elastic movement, one with respect to the other, to thereby provide an adjustable wearable coil structure that can be fitted to the shape of the skull of the treated subject.

One or more support members, 16a and 16b, can be used to mount the wiring assembly 15 above the wound wings/ lobes 11 and 12, and define height H1 (e.g., about 1.5 to 2.5 cm) of the air gap 16g between the applicatory and remote portions of the coils. In some embodiments the electromagnetic butterfly-shaped coil 10 is contained in a helmet (shown in FIG. 14), which can be connected by a suitable cable to an external signal source (e.g., neurostimulator). The helmet is configured in some embodiments to receive a flow of cooling fluid/gas (e.g., cooled air) via one or more inlets, and stream the cooling fluid/gas through the air gap 16g and along, and/or in-between, windings of the wound wings/lobes 11 and 12 mounted inside the helmet to maintain a desired working temperature range of the coils and prevent overheating.

In operation, the wound wings/lobes 11 and 12 are placed over upper portion of the head of the treated subject for positioning each wound wing/lobe over upper lateral sides of the parietal bone. Electric currents are generated by a signals source (83 in FIG. 14) and passed through the wound wing/lobes 11 and 12 can be then used to induce electromagnetic fields directed to specific medial brain regions to affect electric stimulations responsive to respective electric fields evolving therein.

FIG. 2 is a back view of the butterfly-shaped electromagnetic coil assembly 10, showing attachment of the shielding element 13 to inner portions of the domed-shaped wings/lobes 11 and 12. As also seen in FIG. 3, the shielding element 13 comprises two cross-shaped lateral shields, 13a and 13b, each having two arms extending in horizontal sideway directions and two arms vertically extending in superior-inferior directions. Each lateral shield, 13a and 13b, is configured to fit into a respective dome-shaped wound wing/lobe, 11 and 12, and they are connected by their upper arms at an apex area 13x of the shielding element 13. A plurality of perforations can be distributed along the arms of the lateral shields 13a and 13b for passage of cooling fluid/gas therethrough. A "V"-shaped strap shield 13c can be used for connecting between frontal arms of the lateral shields 13a and 13b.

As seen in FIG. 2, the wiring assembly 15 comprises back side openings 15x' and 15y', which communicate via respective pass-through channels formed thereinside with the front side openings (15x and 15y). The wiring assembly 15 may include an addition back side opening 15z', communicating via a respective pass-through channel with a front side opening (15z), configured for passing one or more wires (not shown) therethrough for electrical connection to the temperature sensor 14.

Figure 4:
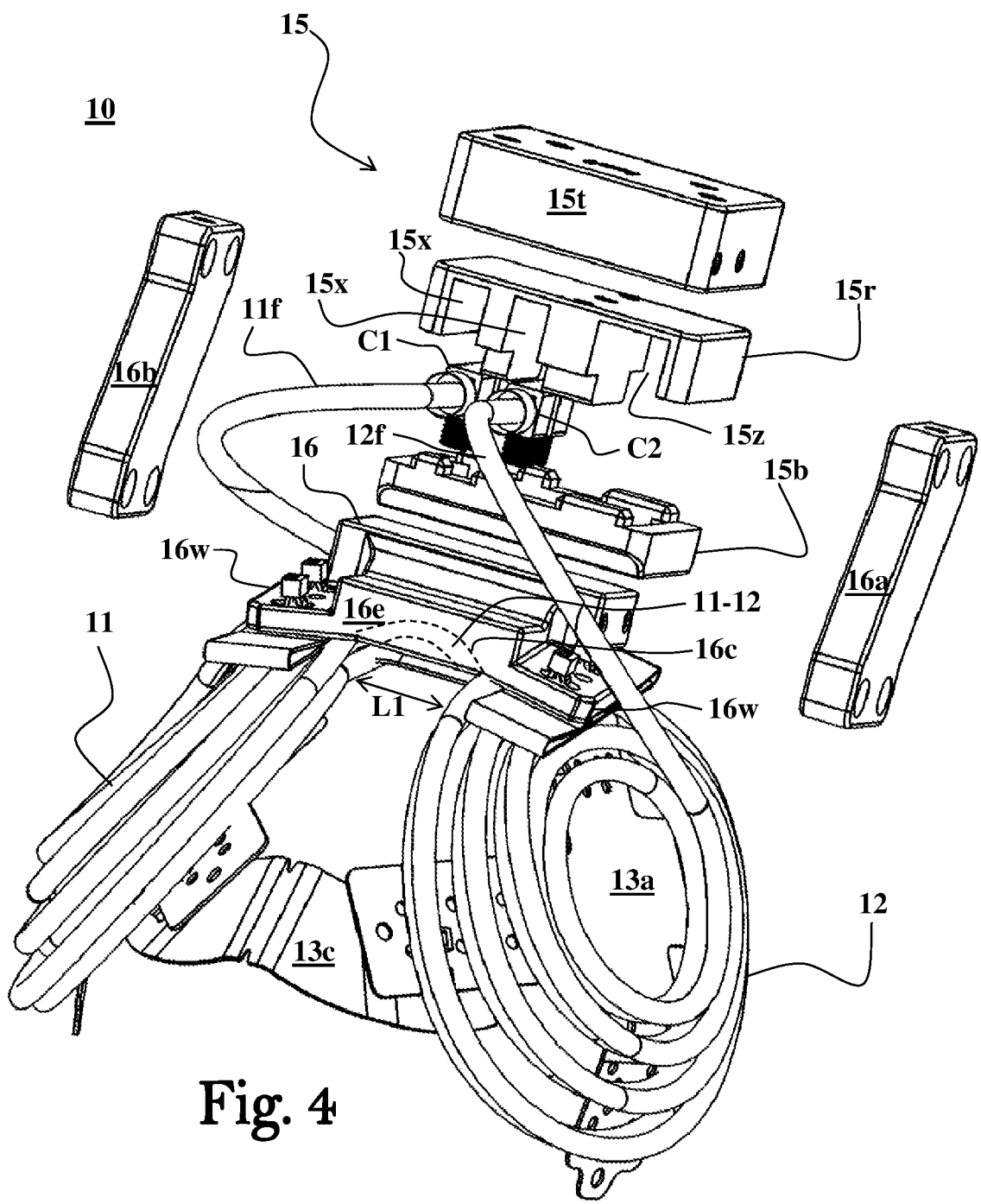
FIG. 4 schematically illustrates an exploded perspective view of the butterfly-shaped electromagnetic H-coil assembly.

FIG. 4 is an exploded perspective view of the butterfly-shaped electromagnetic coil assembly 10 showing elements of the wiring assembly 15 comprising a top shell element 15t, a bottom shell element 15b, and an intermediate element 15r comprising open channels formed in a bottom side thereof and passing from font to back sides thereof. When assembled together, the top shell 15t is attached (e.g., by screws) to the bottom shell 15b, sandwiching the intermediate element 15r therebetween, to thereby close the open channels formed in the intermediate element 15r and form the front sides openings (15x, 15y and 15z) and the back sides openings (15x', 15y' and 15z').

The fastening structure 16 comprises in some embodiments a base portion 16e, and two flat wings 16w, laterally extending from the base portion 16e. The wings 16w can be slightly tilted downwardly with respect to the base portion 16e. The orientation of the wings 16w can be configured to define a desired tilt angle between wound wings/lobes 11 and 12. The flat wings 16w comprise pass-through holes used for attaching superior regions of the wound wings/lobes thereto (e.g., by strip fasteners, cable ties). In some embodiments the fastening structure 16 comprises a channel or slit 16c configured to receive and hold the intermediate wire segment 11-12 connecting between the two wound wings/lobes, 11 and 12. The distance L1 between the wound wings/lobes 11 and 12 at their superior regions can be about 1.5 to 2.5 cm.

Optionally, and in some embodiments preferably, the support members, 16a and 16b, have a slanted structure configured for mounting the wiring assembly 15 posterior to the wound wings/lobes 11 and 12. With this configuration, when mounting the coil assembly 10 in a helmet housing/structure (not shown), the wiring assembly 15 is connected to the helmet such that the wound wings/lobes 11 and 12 can be attached comfortably to a medial head region of the treated subject.

Figure 5:
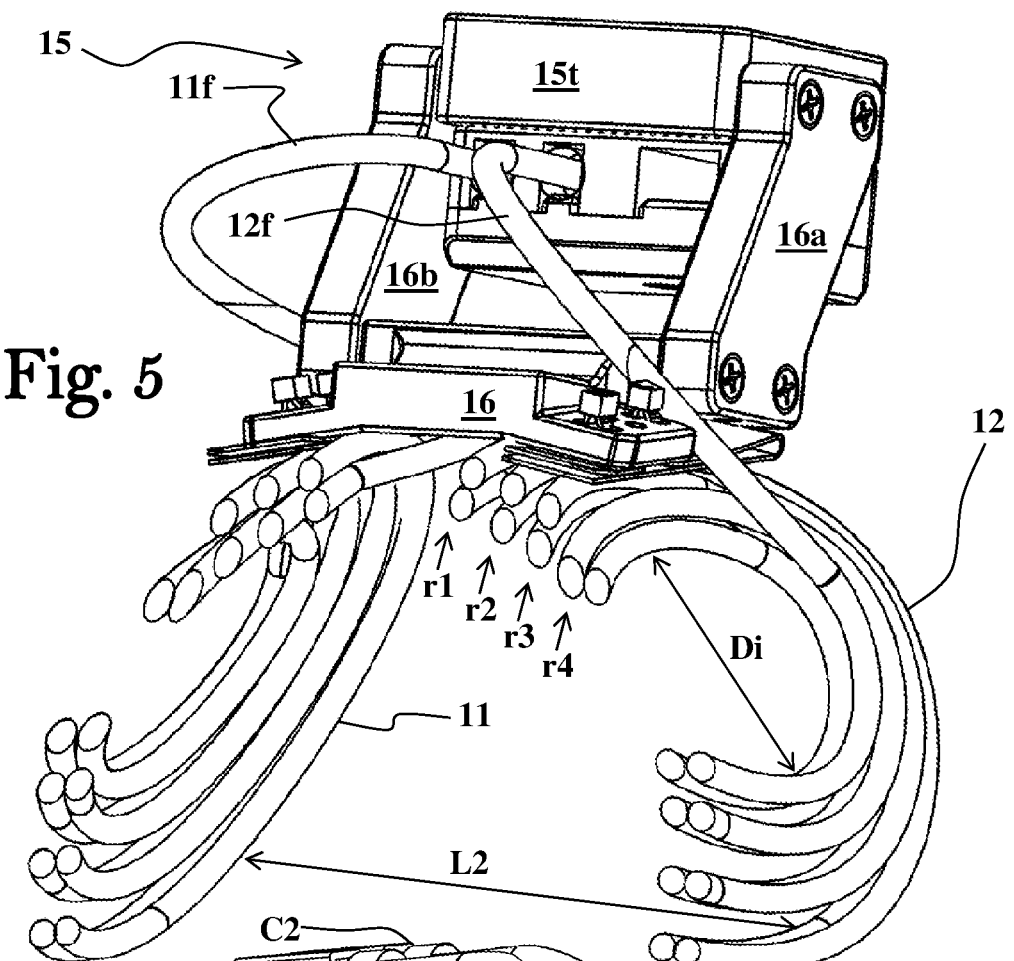
FIG. 5 shows a sectional view of the wound wings/lobes of the electromagnetic H-coil assembly.
Figure 6:
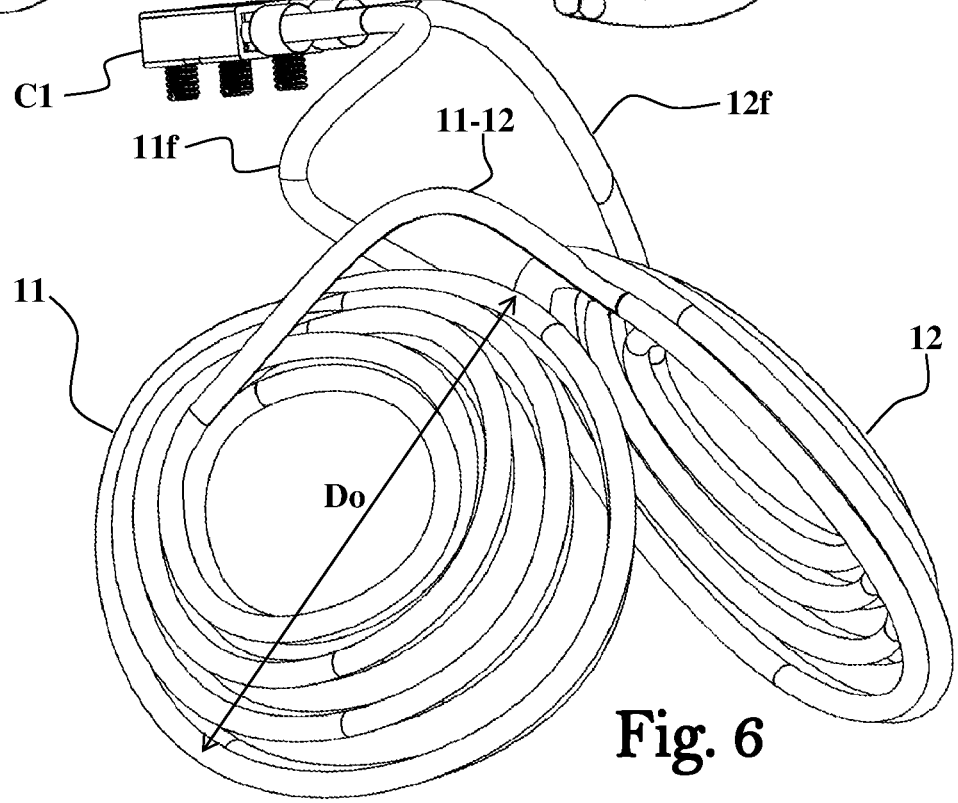
FIG. 6 shows a perspective view of the wound wings/lobes of the butterfly-shaped electromagnetic H-coil assembly FIG. 7 schematically illustrates a front perspective view of an electromagnetic H-coil assembly according to some possible embodiments.

FIG. 5 shows a sectional view of the wound lobes 11 and 12 according to some possible embodiments. The windings/loops of lobs can be arranged in two or more serially connected groups r1, r2, . . . , of concentric windings/loops, wherein the winding/loops of each group having substantially a same diameter. In some possible embodiments the wound lobes 11 and 12 are formed by elliptic windings/loops, and the concentric windings/loops of each group of the two or more serially connected groups r1, r2, . . . , are having substantially same major and minor axes. In this configuration each wing/lobe of loops/windings is made of respective two or more concentric serially connected rings/groups, where each ring/group comprises two or more wire turns and a distance between adjacently located rings/groups is about 0.3 to 1 cm. In this specific example each concentric ring/group r1, r2, . . . , comprises a pair of windings/loops. As seen in FIGS. 5 and 6, each wound wing/lobe 11 and 12 can have an innermost diameter Di, of about 7 to 7.5 cm, defined by one of its innermost windings/loops, and an outermost diameter Do, of about 12 to 14 cm, defined by one of its outermost windings/loops. The distance L2 between the wound wings/lobes 11 and 12 at their inferior regions can be about 16 to 18 cm.

The present application provides in some embodiments electromagnetic H-coils that can be effectively used to apply deep transcranial magnetic stimulation (dTMS) for treating a large variety of psychiatric and neurological conditions with identifiable brain targets. These coils assemblies can be used for the treatment of depressive episodes in patients suffering from major depressive disorder (MDD), episodes of bipolar depression in subjects suffering from bipolar 1 (BP1) or bipolar 2 (BP2) disorders, negative symptoms and cognitive deficit in patients suffering from schizophrenia, depressive episodes in patients suffering from major depressive disorder (MDD) as an-add on to antidepressant medications, and/or post-traumatic stress disorder (PTSD).

FIG. 7 shows a top perspective view of an H-coil assembly 70 according to some possible embodiments. The H-coil assembly 70 is generally arranged to form a helmet structure configured to fit over a head of a treated subject, and comprises a plurality of windings/loops D and P, a shielding element 73 configured to provide structural stability to the windings/loops, and a support structure comprising reinforcing elements comprising a fastening structure 72. Each winding/loop D and P of the H-coil assembly 70 comprises an applicatory portion A, an elevated portion E located above and substantially remote from the applicatory portion A, and one or more intermediate portions M electrically connecting between respective applicatory and elevated portions of the windings/loops. The wires in the applicatory portion A of the windings/loops are configured to form a semi-spherical structure capable of flexibly/elastically fitting over the head of the treated subject. The wires in the intermediate portion M extend vertically upwardly towards the elevated portion E, and the wires in the elevated portion E pass in parallel transversal planes above the applicatory portion A.

These structures of the windings/loops of the H-coil assembly 70 substantially prevents interferences that the electromagnetic fields generated by the wires in the intermediate (M) and elevated (E) portions may cause, thereby allowing directing the electromagnetic fields generated by the wires in the applicatory windings/loops portion (A) substantially accurately to specific regions of the treated subject's head. In addition, placing the elevated windings/loops portions E remote from the applicatory windings/loops portions A forms a wide passage between them through which a coolant gas or fluid (e.g., air) can be streamed for cooling the windings/loops of the H-coil assembly 70.

Optionally, and in some embodiments preferably, the H-coil assembly 70 comprises one or more temperature sensors 71 coupled to wire(s) in the applicatory portion A. In this specific and non-limiting example a single temperature sensor 71 is used to measure the temperature in a region of the applicatory portion A wherein wires of the windings/loops are crossing each other and/or densely arranged one adjacent the other. Such regions are expected to develop more heat relative to the other regions of the applicatory region A as they densely populated by wires of the P and D windings/loops.

The H-coil assembly 70 comprises one or more medial windings/loops D which applicatory portions A configured to traverse medial regions of the assembly, and one or more peripheral windings/loops P configured to traverse peripheral regions of the assembly. As seen in FIG. 7, frontal sections of the peripheral windings/loops P is at least partially crossing over wire segments of the windings/loops of the medial portion D. In this example these frontal sections of the peripheral windings/loops P are arced upwardly and passes over the wire segments of the windings/loops of the medial portion D. As also seen in FIG. 7 the fastening structure 72 comprises two frontal openings, n1 and n2, configured to receive the elevated portions E of the medial windings/loops D for fastening thereinside, and two lateral openings, n3 and n4, configured to receive the elevated portions E of the peripheral windings/loops D for fastening thereinside.

FIG. 8 schematically illustrates a possible embodiment of the shielding element 73. In this embodiment the shielding element 73 comprises a main shielding body 73a configured to cover frontal and one lateral side areas of the subject's head, and a separate side shield 73b configured to cover another lateral side area of the subject's head. The shield parts, 73a and 73b, of the shielding element 73 are made as separated elements in order to increase the flexibility of the coil assembly 70, and in order to ease the winding process of the electromagnetic coil. The main shielding body 73a comprises two inverted "T"-shape structures connected to each other at the apex region 73x, and the side shield 73b is made of a single inverted "T"-shape structure, each of said inverted "T"-shape structures comprises curved base and neck sections. The main shielding body 73a comprises the base section 73f configured for placement over an area of the subject's forehead, a 'neck' section arcing upwardly from the base section 73f to merge at the apex 73x with the downwardly arcing 'neck' section of the base portion 73g, configured to cover a left side area of the subject's head. The side shield 73b comprises a base section 73e configured to cover a left side area of the subject's head, and a 'neck' section arcing upwardly, but which do not connect to the apex region 73x. The shielding element 73 comprises a plurality of perforations 73n configured to permit passage of a coolant therethrough towards, or from, the wires of the windings/loops.

Figure 9:
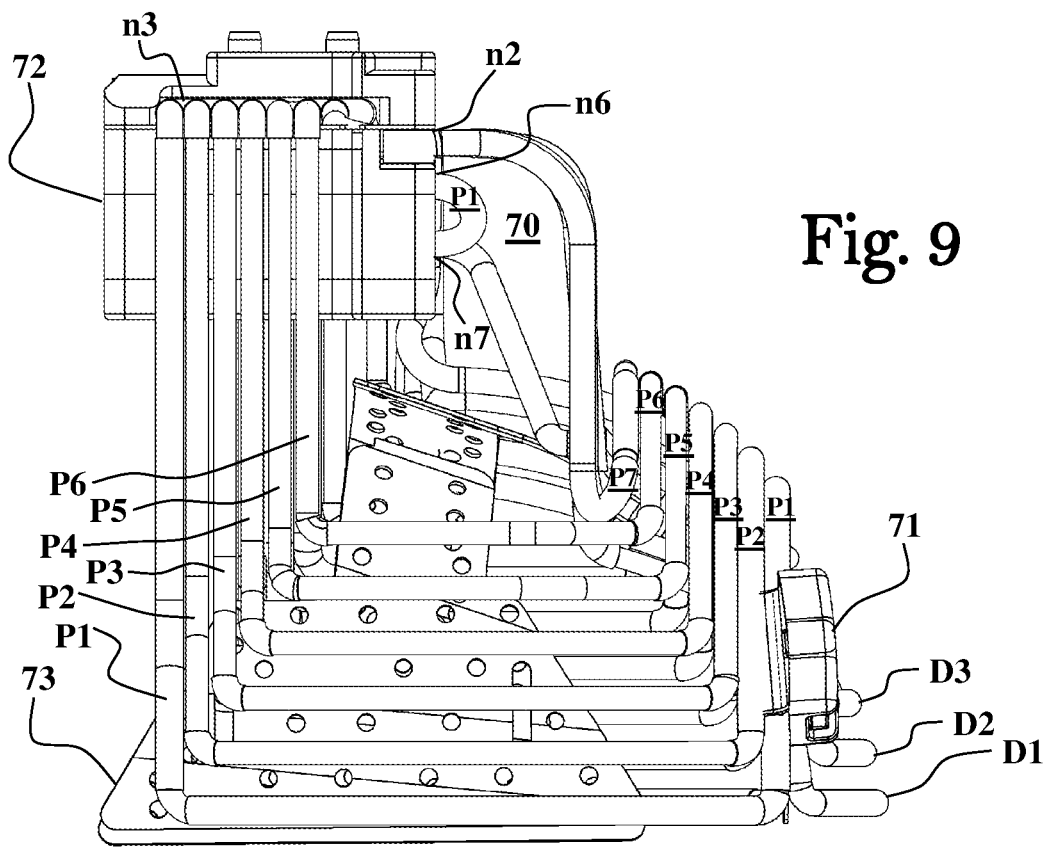
FIGS. 9 and 10 show side views of the electromagnetic H-coil assembly according to some possible embodiments.

FIG. 9 is a left-side view of the coil assembly 70, showing wire segments of the applicatory portion (A) that pass over fontal and right side areas of the subject's head. In some embodiments the coil assembly comprises seven peripheral windings/loops P1, P2, P3, P4, P5, P6, and P7 (collectively referred to herein as peripheral windings/loops P). Each of the peripheral windings/loops P define a different diameter in the structure forming the semi-spherical structure of the coil assembly, where P1 is the lowermost winding/loop, and P7 is the uppermost winding/loop, and the windings are arranged one above the other in a descending order of their diameters.

At the frontal area the peripheral windings/loops P1, P2, P3, P4, P5, P6, and P7, are arced upwardly and pass/cross over the medial windings/loops D1, D2, . . . (collectively referred to herein as medial windings/loops D), the peripheral windings/loops P1, P2, P3, P4, P5 and P6, extend from the frontal area along a distance traversing the right side of the subject's head, while the peripheral winding/loop P7 extends from the frontal area upwardly and curved into the opening n2 of the fastening structure 72, where it serially connects the peripheral windings/loops P to the medial windings/loops D. From the posterior right side of the subject's head the peripheral windings/loops P1, P2, P3, P4, P5 and P6, extend upwardly and curved into the side opening n3 of the fastening structure 72.

Figure 10:
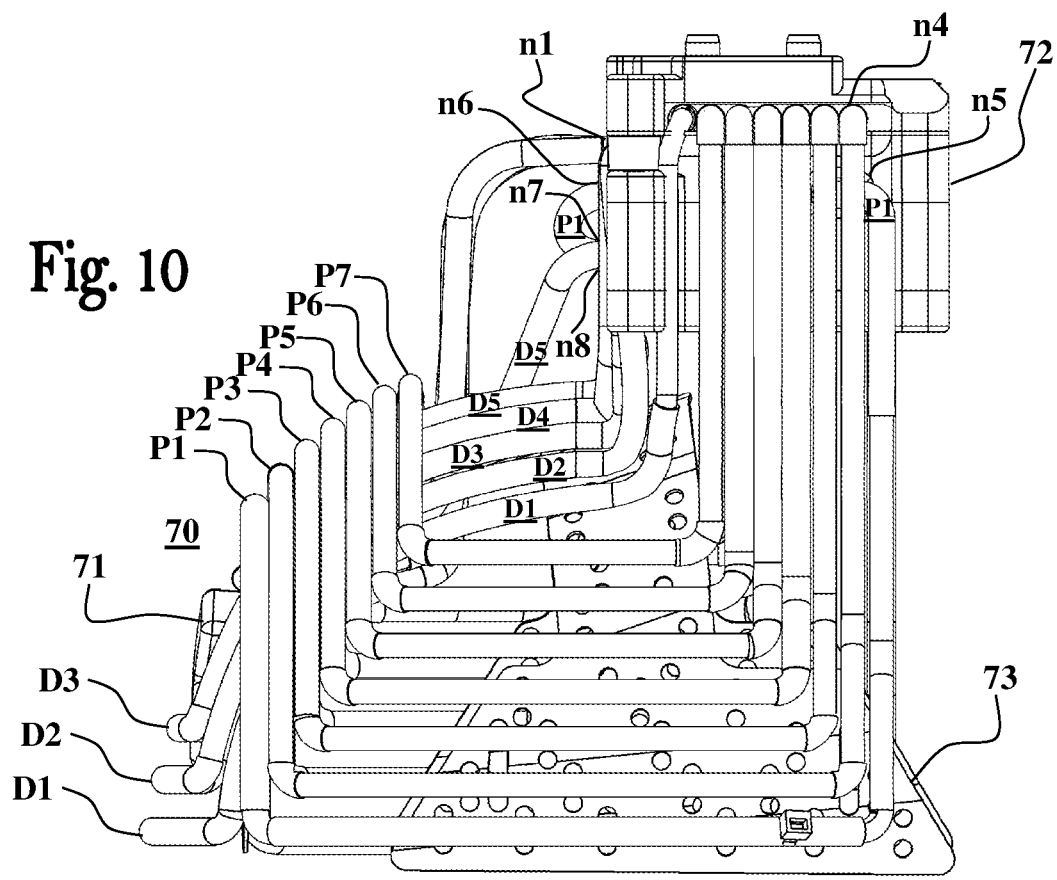

FIG. 10 is a right-side view of the coil assembly 70, showing wire segments of the applicatory portion (A) that pass over fontal and left side areas of the subject's head. As seen, the peripheral windings/loops P2, P3, P4, P5, P6, and P7, are curved out from the side opening n4 of the fastening structure 72, and the peripheral winding/loop P1 is curved out from an additional side opening n5 located below the side opening n4. The free end of the peripheral winding/loop P1 is introduced via the additional side opening n5 into the fastening structure 72, diagonally traverses a distance inside the fastening structure 72 and emerges out via the frontal opening n6, wherefrom it is curved to enter back into the fastening structure 72 via a lower frontal opening n7 wherein it is electrically connected to a connector element (C2 in FIG. 11). The peripheral windings/loops P1, P2, P3, P4, P5, P6, and P7, extend downwardly from their respective side openings towards a posterior left side of the subject's head, and therefrom extend a distance traversing the left side of the subject's head. At the frontal area of the subject's head the peripheral windings/loops P are arced upwardly over/across the medial windings/loops D.

In some embodiments the coil assembly 70 comprises five medial windings/loops D1, D2, D3, D4, and D5, where D1 is the lowermost medial winding/loop, and D5 is the uppermost medial winding/loop. The medial windings/loops D1, D2, D3, D4, and D5, are arranged one above the other in a descending order of diameters of the semi-spherical structure thereby defined. As seen in FIG. 10, portions of the medial windings/loops D1, D2, D3, D4, and D5, extend along a distance traversing an upper left side area of the subject's head. In this configuration the left side of the subjects head is substantially covered by wire segments of the peripheral loops P and of the medial loops D. More particularly, a lower region of the left side of the subject's head is covered by the peripheral windings/loops P1, P2, P3, P4, P5, P6, and P7, and an upper region of the left side of the subject's head is covered by the medial windings/loops D1, D2, D3, D4, and D5.

Figure 11:
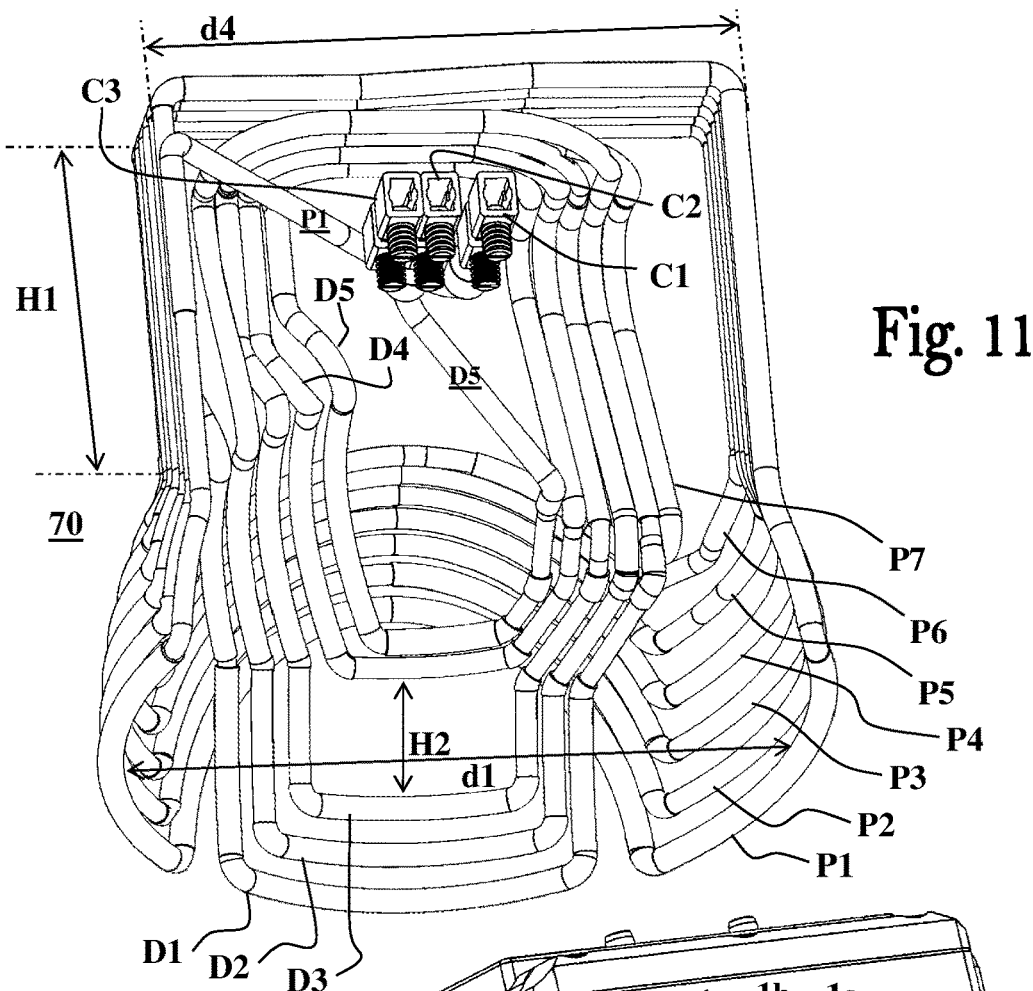
FIG. 11 shows a back perspective view showing the windings/loops of the electromagnetic H-coil assembly according to some possible embodiments.

FIG. 11 is a back perspective view of the H-coil assembly 70 without the fastening structure (72) and the shielding element (73), showing the different windings/loops and the connector elements C1, C2 and C3, located inside the fastening structure (72). As seen, the free remote end portion of the peripheral winding/loop P1 is connected (inside the fastening structure 72) to the connector element C2, and the medial winding/loop D5 is connected (inside the fastening structure 72) to the connector element C1. The additional connector element C3 is used for connecting wire(s) to the temperature sensor (71). Fastening structure (72) is configured in some embodiments to provide passage of the wires in several parallel transverse planes. In an upper transverse plane the wires in the elevated portion of the peripheral windings/loops P2, P3, P4, P5, P6, and P7, are passed substantially aligned and parallel one to the other, in a middle transverse plane the wires in the elevated portion of the medial windings/loops D2, D3, D4 and D5, are passed in an arced interfolded form, and in a lower transverse plane the free remote end wire portion of the peripheral winding/loop P1 is diagonally passed for connecting it to the connector element C2, whereas the connector elements C1, C2 and C3, are located below the lower transverse plane of the fastening structure (72). This configuration thus provides reduced magnetic coupling between the wires passing in the different transverse planes, by arranging the wires passing therethrough in different plane orientations.

In some embodiments the coil assembly 70 comprises one or more upper-medial windings/loops which applicatory portions are configured to traverse upper-medial regions of the subject's head, and one or more lower-medial windings/loops which applicatory portions are configured to traverse lower-medial regions of the subject's head. In this specific and non-limiting embodiment there are three lower-medial windings/loops D1, D2 and D3, and two upper-medial windings/loops D4 and D5. Frontal segments of the lower-medial windings/loops D1, D2 and D3, are configured to pass over an area of the forehead of the subject, and frontal segment of the upper-medial windings/loops D4 and D5 pass above the lower-medial windings/loops D1, D2 and D3, in a distance H2 of about 2.5 to 3 cm.

A diameter dl defined by the lowermost peripheral winding/loop P1 can be configured for flexibly fitting the coil assembly over heads of different sizes. In some embodiments the diameter dl of the lowermost peripheral winding/loop P1 is about 10 to 13 cm. In this configuration the distance d4 of the elevated wires of the peripheral windings/loops P2, P3, P4, P5, P6, and P7 transverse can be about 11 to 13 cm, and the elevation H1 of the elevated portions of the windings/loops can be about 8 to 10 cm.

Figure 12:
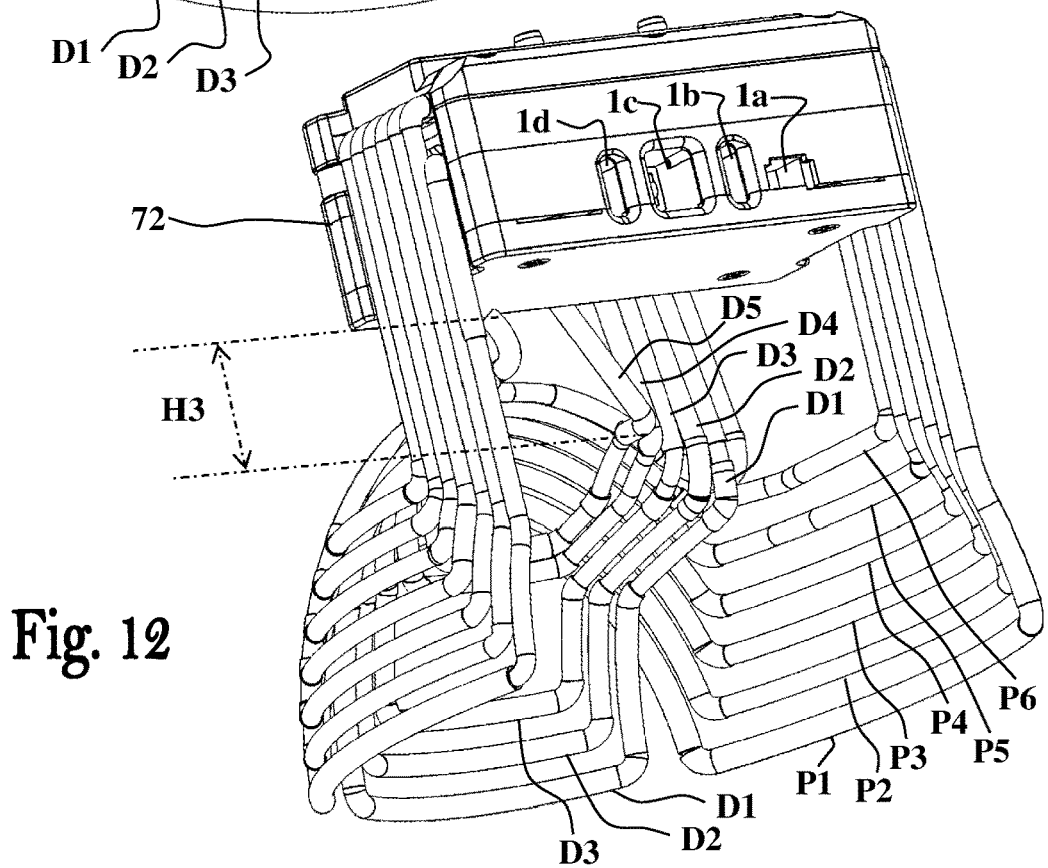
FIG. 12 shows a back perspective view of a fastening structure used for reinforcing the windings/loops of the H-coil according to possible embodiments.

FIG. 12 is a back perspective view of the H-coil assembly 70 without the shielding element (73), but with the fastening structure (72), showing four back openings 1a, 1b, 1c and 1d, configured to provide access for wiring a cable (not shown) to the fastening structure 72. The back opening 1a is configured to provide access to the connector element C3, for the temperature sensor, the back opening 1c is configured to provide access to the connector element C1, and the back opening 1b is configured to provide access to the connector element C2. Placing the elevated portions of the loops remote from the applicatory portions forms an air gap H3, of about 3 to 4 cm, that can be advantageously used for streaming a coolant to/or from the applicatory portions of the loops, and thereby enable using temperature control techniques to prevent overheating.

In some embodiments a sham coil (not shown) is placed adjacent and above the wires of the main electromagnetic H-coil e.g., inside the helmet. The sham coil is configured to produce acoustic artifact similar to that produced by the active electromagnetic H-coil, but without effecting any actual brain stimulation. In such embodiments the back opening 1d is configured to provide access to a power connection (not shown) of the sham coil. This setup is used in some embodiments for double blind placebo-controlled (DBPC) clinical trials. In such trials the system can be configured to selectively connect either the main electromagnetic coil or the sham coil to the stimulator, based on a unique identification token (e.g., magnetic card) of the treated subject, such that both the treated subject and the operator are adequately blinded to the mode of treatment conducted by the system.

Figure 13:
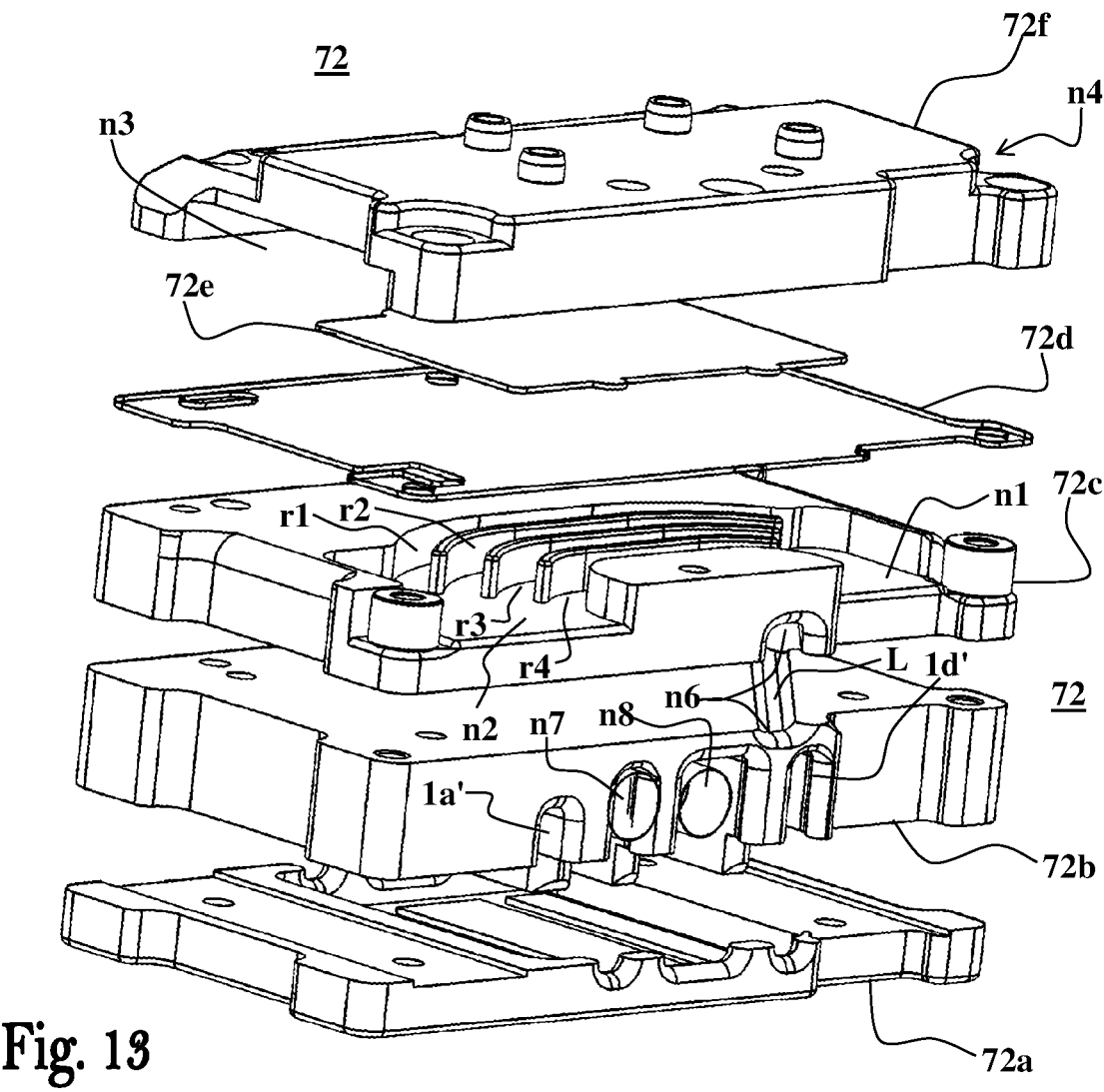
FIG. 13 shows an exploded perspective view of a fastening structure for the H-electromagnetic coil according to some possible embodiments.

FIG. 13 is a perspective exploded view of the fastening structure 72 of some possible embodiments. In this embodiment the fastening structure 72 comprises top and bottom shell elements, 72f and 72a respectively, and first and second intermediate elements, 72c and 72b, located one on top the other and between the top and bottom shell elements, 72f and 72a. The top shell element 72f is configured to construct the lateral openings, n3 and n4, and an elongated channel passing between them configured for holding the elevated portions of the peripheral windings/loops. A partitioning element 72e can be used in some embodiments as an insulation layer located above the wire segments of the remote portion of the peripheral windings/loops and beneath the top shell element 72f, in order to electrically insulate between the windings and metal screws (not shown) in the shell element 72f. In some embodiments these metal screws are also used to connect the coil assembly to the helmet structure.

The first intermediate element 72c is configured to connect to the top shell element 72f, and thereby define the two frontal openings, n1 and n2. The first intermediate element 72c comprises a plurality of arc-shaped channels e1, e2, e3 and e4, each configured to hold a wire segment of an elevated portion of a medial winding/loop. A partitioning element 72d placed over the wire segments of the elevated portions of the medial winding/loop held inside the arc-shaped channels e1, e2, e3 and e4, can be used to separate/insulate between the elevated portions of the medial windings/loops and the elevated portions of the periphery windings/loops.

The bottom surface of the first intermediate section 72c, and the upper surface of the second intermediate section 72b, each comprises diagonal slit used to construct a diagonal channel L, and the frontal opening n6, used for passage of the free end remote portion of the peripheral winding/loop P1, when the first and second intermediate sections are attached one to the other. The second intermediate section 72b comprises a plurality of open channels formed in its bottom side and passing all the way from the front to the back side, configured for holding the connector elements. The bottom shell element 72a is configured to construct the front openings, 1a', n7, n8, 1d', and to close the open channels formed in the bottom side of the second intermediate element 72b, when attached to the second intermediate element 72b. The open channels passing through the second intermediate section 72b communicate between the front side openings 1a', n7, n8 and 1d', and the respective back side openings (1a, 1b, 1c and 1d).

Figure 14:
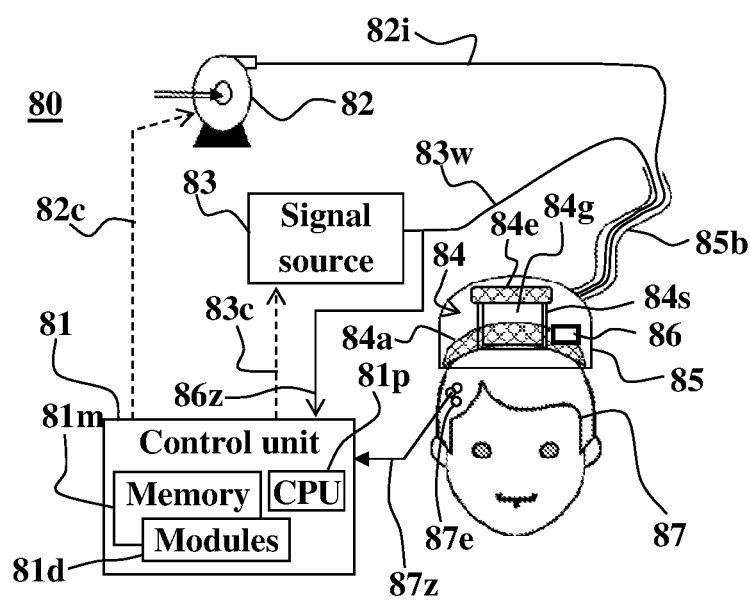
FIG. 14 schematically illustrates a brain stimulation system according to some possible embodiments.

FIG. 14 schematically illustrates a brain stimulation system 80 according to some possible embodiments. The brain stimulation system 80 comprises a coil assembly 84 configured to fit over a head region of a treated subject 87, a signal generator (e.g., neurostimulator) 83 configured to drive the coil assembly 84 with electric signals for inducing electromagnetic fields inside the subject's head 87, an electric pump 82 configured to stream a coolant to the coil assembly 84, and a control unit 81 configured and operable to operate the pump 82 and signal generator 83. The coil assembly 84 comprises an applicatory coil portion 84a configured to fit over a head region of the subject 87 and induce the electromagnetic fields thereinto, an elevated coil portion 84e located relatively remote to the applicatory coil portion 84a, and a support structure 84s configured to enclose and hold some portion of the windings/loops of the coil assembly 84 while enabling elastic movement of other portions of the windings/loops to enable adjusting a geometrical dimension of the coil assembly 84 for fitting it over the head region of the treated subject 87. The support structure 84s is further configured to support the elevated coil portion 84e at some predefined distance from/above the applicatory coil portion 84a, to prevent interference of electromagnetic fields thereby produced with the electromagnetic fields produced by the applicatory coil portion 84a, and for maintaining an air gap 84g between the applicatory and elevated coil portions, 84a and 84e respectively, and for streaming the coolant (e.g., cooling gas/fluid) from the pump 82 to cool the coil assembly 84. The support structure 84s comprises in some embodiments the fastening structure and/or the wiring assembly/structure described hereinabove.

The coil assembly 84 can be enclosed inside a wearable structure (e.g., a helmet) 85 configured to fit over the subject's head 87. The wearable structure 85 comprises a cable assembly 85b configured to communicate electric signals and cooling media with the coil assembly 84. The cable assembly 85b comprises a fluid conduit 82i configured to stream the cooling media from the pump 82 to the coil assembly 84, and various electrical conductors 83w for communicating electric signals with the coil assembly 84, such as electrical signals from the signal generator 83 for operating the coil assembly 84. In some embodiments the coil assembly 84 comprises a sensor device 86 configured to measure at least one property or condition associated with the operational coil portion 84a, and generate signals/data 86z indicative thereof. Accordingly, the electrical conductors 83w of the cable assembly 85b can also communicated the signals/data 86z from the sensor device 86 to the control unit 81. Optionally, but in some embodiments preferably, the sensor device 86 comprises at least one temperature sensor configured to measure temperature of windings/loops of the applicatory coil portion 84a.

The control unit 81 comprises one or more processors 81p and memories 81m, configured and operable to execute one or more program modules 81d for operating the coil assembly 84. The control unit 81 can be configured to process the measurement signals/data 86z from the sensor device 86, generate control signals 82c for activating the pump 82 to stream the cooling media through the conduit 82i at a certain rate based on the measurement signals/data 86z, and/or generate control signal 83c for operating the signal generator 83 for generating electrical signal supplied to the coil assembly for inducing electromagnetic fields inside the head of the treated subject 87. In some embodiments one or more sensor elements (e.g., EEG electrodes) 87e attached to the subject's head 87 are used to measure electrical activity of the subject's brain and generate signals/data 87z indicative thereof. The control unit 81 can be configured to process the signals/data 87z generated by the sensor elements 87e and responsively generated control signals 82c for adjusting the signals generated by the signal generator 83, accordingly.

Terms such as top, bottom, front, back, right, and left and similar adjectives in relation to orientation of the elements and components shown in the figures refer to the manner in which the illustrations are positioned on the paper, should not impose limitations to the orientations in which the they can be used in actual applications. As described hereinabove and shown in the associated figures, the present application provides electromagnetic coil configurations usable for treating a subject by inducing electromagnetic fields inside head regions thereof e.g., employing dTMS/deep rTMS procedures. While particular embodiments of the invention have been described, it will be understood, however, that the invention is not limited thereto, since modifications may be made by those skilled in the art, particularly in light of the foregoing teachings. As will be appreciated by the skilled person, the invention can be carried out in a great variety of ways, employing more than one technique from those described above, all without exceeding the scope of the claims.

The invention claimed is:

1. An electromagnetic coil assembly for inducing electromagnetic fields inside a head region of a treated subject, the electromagnetic coil assembly comprising:
   a plurality of windings configured to define an applicatory coil portion comprising two domed-shaped coil structures electrically connected by an intermediate wire and configured to define a semi-spherical volume for placement in close proximity to a head of the treated subject and fitting over a region of the head of the treated subject to induce the electromagnetic fields, and an elevated coil portion configured to pass relatively remote from the head of the treated subject and configured such that electromagnetic fields thereby produced are generated substantially remote from the head of the treated subject to prevent the electromagnetic fields from interfering with the electromagnetic fields generated by the applicatory portion of the electromagnetic coil assembly, thereby allowing directing the electromagnetic fields generated by the applicatory coil portion substantially accurately to desired inner regions of the head of the treated subject;
   a support structure configured to enclose and immobilize at least a portion of the plurality of windings of the coil assembly, while enabling elastic movement of other portions of the plurality of windings that are not held by the support structure, to thereby enable size adjustment of the electromagnetic coil assembly to fit over the region of the head of the treated subject, wherein the support structure is attached to superior sections of said two dome-shaped coil structures to thereby permit elastic movement of said two dome-shaped coil structures in sideway directions; and
   an air gap formed with the support structure to maintain an open passage between the applicatory coil portion and the elevated coil portion for streaming cooling media along or in-between windings of the applicatory coil portion.

2. The electromagnetic coil assembly of claim 1 wherein the electromagnetic coil assembly is made from a wire having cross-sectional area of about 7 to 10 $mm^2$, a length of about 500 to 800 cm, and a total electrical resistance of about 0.01 to 0.04 Ohm.

3. The electromagnetic coil assembly of claim 1 wherein the plurality of windings of the coil assembly have an inductance of about 13 to 20 μH.

4. The electromagnetic coil assembly of claim 1 wherein the windings of the applicatory coil portion are configured and operable to generate an electromagnetic field in a range of 0.05 to 2 Tesla inside the head of the treated subject, and establish an electric field of about 100 to 200 V/m at a distance of about 0.5 to 3 cm from said windings.

5. The electromagnetic coil assembly of claim 1 wherein the support structure includes a wiring assembly located above and relatively remote to the two dome-shaped coil structures and configured to receive and hold the elevated coil portion and to thereby define the air gap between said elevated coil portion and said two dome-shaped coil structures, said air gap configured for directing the cooling media therethrough for cooling the two dome-shaped coil structures.

6. The electromagnetic coil assembly of claim 1, further comprising one or more temperature sensors coupled to at least one of the two dome-shaped coil structures.

7. The electromagnetic coil assembly of claim 1 wherein each of the two dome-shaped coil structures comprises an innermost loop, an outermost loop, and at least one wire segment spiraling between said innermost and outermost loops.

8. The electromagnetic coil assembly of claim 7 wherein the intermediate wire is configured to connect between an innermost loop in one of the two dome-shaped coil structures and an outermost loop in the other dome-shaped coil structure, and wherein the at least one wire segment spiraling between said innermost and outermost loops of said two dome-shaped coil structures is spiraling in opposite directions.

9. The electromagnetic coil assembly of claim 7 wherein a diameter of the innermost loop is in a range of 7 to 7.5 cm.

10. The electromagnetic coil assembly of claim 7 wherein a diameter of the outermost loop is in a range of 12 to 14 cm.

11. The electromagnetic coil assembly of claim 7 wherein each of the two dome-shaped coil structures comprises groups of concentric loops, each loop comprising two or more concentric windings having substantially a same diameter.

12. The electromagnetic coil assembly of claim 11 wherein a spacing between adjacently located groups of concentric loops is in a range of 0.3 to 1 cm.

13. The electromagnetic coil assembly of claim 7 wherein loops of the two dome-shaped coil structures have an elliptic shape, wherein major and minor axes of the innermost loops are about 6.5 to 7.5 cm and 7.5 to 9 cm, respectively, and the major and minor axes of the outermost loops are about 11 to 13 and 13 to 15 cm, respectively.

14. The electromagnetic coil assembly of claim 1 wherein the support structure comprises a fastening structure configured to hold and immobilize the superior sections of the dome-shaped coil structures and maintain an angle of about 120° to 140° between said dome-shaped coil structures.

15. The electromagnetic coil assembly of claim 14 wherein a distance between the two dome-shaped coil structures is in a range 2 to 7 cm.

16. The electromagnetic coil assembly of claim 14 wherein a distance between the superior sections of the two dome-shaped coil structures is in a range of 1.5 to 2.5 cm.

17. The electromagnetic coil assembly of claim 14 wherein a distance between inferior sections of the two dome-shaped coil structures is in a range of 16 to 18 cm.

18. The electromagnetic coil assembly of claim 14 wherein the support structure includes a wiring assembly located above and relatively remote to the two dome-shaped coil structures, and wherein the support structure comprises one or more support members configured to attach the wiring assembly to the fastening structure and maintain the air gap therebetween, and wherein the one or more support members have a slanted configuration configured to mount the wiring assembly posterior to the two domed-shaped coil structures for preventing electromagnetic fields interferences.

19. The electromagnetic coil assembly of claim 1 configured for mounting inside a helmet structure.

20. An electromagnetic coil assembly for inducing electromagnetic fields in a head region of a treated subject, the electromagnetic coil assembly comprising:

a plurality of windings configured to define an applicatory coil portion configured for placement in close proximity to a head of the treated subject to induce the electromagnetic fields, and an elevated coil portion configured to pass relatively remote from the head of the treated subject and configured such that electromagnetic fields thereby produced are generated substantially remote from the head of the treated subject to prevent the electromagnetic fields from interfering with the electromagnetic fields generated by the applicatory portion of the coil assembly, thereby allowing directing the electromagnetic fields generated by the applicatory coil portion substantially accurately to desired inner regions of the head of the treated subject;

intermediate coil portions electrically connecting the applicatory coil portion to the elevated coil portion passing in a transverse horizontal plane remote from the applicatory portion;

a support structure configured to enclose and immobilize at least a portion of the plurality of windings of the coil assembly, while enabling elastic movement of other portions of the plurality of windings that are not held by the support structure, to thereby enable size adjustment of the electromagnetic coil assembly to fit over a region of the head of the treated subject; and an air gap for with the support structure to maintain an open passage between the applicatory and remote coil portions for streaming cooling media along or in-between windings of the applicatory coil portion, and wherein the electromagnetic coil assembly comprises: one or more medial loops having portions in said intermediate coil portions and said elevated coil portion, the applicatory portion of said one or more medial loops being configured to traverse a medial region of the subject's head; one or more peripheral loops having portions in said applicatory coil portion, said intermediate coil portions and said elevated coil portion, the applicatory portion of said one or more peripheral loops being configured to traverse a peripheral region of the subject's head and thereby at least partially cross a portion of said one or more medial loops; and wherein the support structure is configured to hold and immobilize the elevated portion of said one or more peripheral loops in a first transverse plane and the elevated portions of said one or more medial loops in a second transverse plane substantially parallel to said first transverse plane, while permitting elastic movement in the intermediate coil portions and the applicatory coil portion of the loops.

21. The electromagnetic coil assembly of claim 20 wherein the first transverse plane is located above and adjacent the second transverse plane, and wherein the elevated portion of the one or more peripheral loops passing in said first transverse plane are configured to be substantially parallel to a frontal plane of the treated subject.

22. The electromagnetic coil assembly of claim 20 wherein the elevated portion of each of the one or more medial loops is arc-shaped.

23. The electromagnetic coil assembly of claim 22 wherein the one or more medial loops comprises one or more upper-medial loops having portions in the applicatory coil portion, the intermediate coil portions and the elevated coil portion, the applicatory portion of said one or more upper-medial loops being configured to traverse an upper-medial region of the subject's head, and one or more lower-medial loops having portions in the applicatory coil portion, the intermediate coil portions and the elevated coil portion, the applicatory portion of said one or more lower-medial loops being configured to traverse a lower-medial region of the subject's head.

24. The electromagnetic coil assembly of claim 23, wherein the elevated portions of each of the one or more upper-medial loops and the one or more lower-medial loops is arc-shaped, and wherein the arc-shaped elevated portions of the one or more upper-medial loops are at least partially accommodated in the arc-shaped elevated portion of the one or more lower-medial loops.

25. The electromagnetic coil assembly of claim 24 wherein the support structure comprises a fastening structure comprising two lateral openings connected by an elongated channel configured to accommodate the elevated portion of the one or more peripheral loops, and two frontal openings connected by a plurality of arc-shaped channels passing below said elongated channel and configured to accommodate the elevated portions of said one or more upper-medial and lower-medial loops.

26. The electromagnetic coil assembly of claim 23 wherein wire segments in the applicatory portion of the one or more peripheral loops, the one or more lower-medial loops, and the one or more upper-medial loops are configured to pass over lateral side areas of the subject's head.

27. The electromagnetic coil assembly of claim 26 wherein the one or more peripheral loops, the one or more lower-medial loops, and the one or more upper-medial loops are placed one above the other in a descending order with respect to a diameter defined by each loop.

28. The electromagnetic coil assembly of claim 27 wherein the wire segments that are configured to pass over the lateral side areas of the subject's head are arranged such that the wire segments of the one or more peripheral loops are located below the wire segments of the one or more lower-medial loops, and the wire segments of the one or more lower-medial loops are located below the wire segments of the one or more upper-medial loops.

29. The electromagnetic coil assembly of claim 20, comprising seven peripheral loops and two upper-medial loops.

30. The electromagnetic coil assembly of claim 20 wherein a cross sectional area of a wire of the one or more medial and peripheral loops is in the range of 7 to 10 mm$^2$, and wherein the wire of said one or more peripheral and medial loops is a continuous wire having a length in a range of 700 to 800 cm, and wherein electrical resistance of the coil assembly is in a range of 0.01 to 0.02 Ohm.

31. The electromagnetic coil assembly of claim 30 wherein inductance of the coil assembly is in a range of 19.4 to 19.6 µH, and wherein the applicatory portion of the one or more medial and peripheral loops is configured to generate a magnetic field in a range of 0.4 to 3.2 Tesla deep inside the subject's head.

32. The electromagnetic coil assembly of claim 31 wherein the applicatory portion of the one or more medial and peripheral loops is configured to induce an electric field in the range of 100 to 200 V/m.

33. A helmet for application of transcranial magnetic stimulations, the helmet comprising:
  a wearable housing;
  an electromagnetic coil assembly enclosed inside said housing and comprising a plurality of windings configured to define an applicatory coil portion configured for placement in close proximity to a head of a treated subject to induce electromagnetic fields, and an elevated coil portion configured to pass relatively remote from the head of the treated subject and configured such that electromagnetic fields thereby produced are generated substantially remote from the head of the treated subject to prevent the electromagnetic fields from interfering with the electromagnetic fields generated by the applicatory portion of the electromagnetic coil assembly, thereby allowing directing the electromagnetic fields generated by the applicatory coil portion substantially accurately to desired inner regions of the head of the treated subject;
  a support structure configured to enclose and immobilize at least a portion of the plurality windings of the coil assembly, while enabling elastic movement of other portions of the plurality of windings that are not held by the support structure, to thereby enable size adjustment of the electromagnetic coil assembly to fit over a region of the head of the treated subject;
  an air gap formed with the support structure to maintain an open passage between the applicatory and elevated coil portion for streaming cooling media along or in-between windings of the applicatory coil portion; and
  at least one air inlet configured for receiving the cooling media and streaming said cooling media along and in-between the windings of the coil assembly.

34. The helmet of claim 33, further comprising one or more temperature sensors coupled to one or more wires of the coil assembly in areas that absorb heat substantially produced by the applicatory coil portion.

35. The helmet of claim 33 wherein the electromagnetic coil assembly is made from a wire having a cross-sectional area of about 7 to 10 mm$^2$, a length of about 500 to 800 cm, and a total electrical resistance of about 0.01 to 0.04 Ohm.

36. The helmet of claim 33 wherein inductance of the plurality of windings of the coil assembly is about 13 to 20 µH.

37. The helmet of claim 33 wherein the applicatory coil portion is configured and operable to generate an electromagnetic field in a range of 0.05 to 2 Tesla inside the head of the treated subject, and establish an electric field of about 100 to 200 V/m at a distance of about 0.5 to 3 cm from the windings of the electromagnetic coil assembly.

38. The helmet of claim 33 wherein the electromagnetic coil assembly comprises an intermediate portion electrically connecting between the applicatory and elevated portion while maintaining the air gap between the applicatory and elevated coil portion.

39. A brain stimulation system comprising: the helmet for application of transcranial magnetic stimulations of claim 33; a signal generator configured to drive the coil assembly for inducing the electromagnetic fields inside the subject's head; an electric pump configured to stream the cooling media to the coil assembly; a sensor device configured to measure at least one property or condition associated with the applicatory coil portion and generate measurement data indicative thereof; and a control unit configured and operable to generate signals for operating the pump and the signal generator at least partially based on said measurement data.

40. The brain stimulation system of claim 39, further comprising one or more sensor elements attachable to the subject's head for measuring electrical activity of the subject's brain and generating measured brainwaves data indicative thereof, and wherein the control unit is configured and operable to process said brainwaves data and generate control signals for adjusting activation signals generated by the signal generator.

* * * * *